(12) United States Patent
Jacques et al.

(10) Patent No.: US 11,369,807 B2
(45) Date of Patent: Jun. 28, 2022

(54) COMPACT PROTON THERAPY SYSTEMS AND METHODS

(71) Applicant: ProNova Solutions, LLC, Maryville, TN (US)

(72) Inventors: Aaron Jacques, Knoxville, TN (US); Niek Schreuder, Knoxville, TN (US); Terry Douglass, Knoxville, TN (US); Joseph C. Matteo, Walland, TN (US); Steve Schrick, Lenoir City, TN (US); Jacob Shamblin, Knoxvillle, TN (US); Ian Turnbull, Louisville, TN (US); Yan Zhang, Knoxville, TN (US)

(73) Assignee: ProNova Solutions, LLC, Knoxville, TN (US)

( * ) Notice: Subject to any disclaimer, the term of this patent is extended or adjusted under 35 U.S.C. 154(b) by 60 days.

(21) Appl. No.: 16/740,150

(22) Filed: Jan. 10, 2020

(65) Prior Publication Data

US 2020/0316408 A1 Oct. 8, 2020

Related U.S. Application Data

(60) Provisional application No. 62/790,856, filed on Jan. 10, 2019.

(51) Int. Cl.
*A61N 5/10* (2006.01)
(52) U.S. Cl.
CPC ......... *A61N 5/1079* (2013.01); *A61N 5/1037* (2013.01); *A61N 5/1069* (2013.01);
(Continued)

(58) Field of Classification Search
CPC .. A61N 5/1079; A61N 5/1081; A61N 5/1049; A61N 5/1069; A61N 5/1037;
(Continued)

(56) References Cited

U.S. PATENT DOCUMENTS 5,168,514 A 12/1992 Horton, Jr. et al.
5,349,198 A 9/1994 Takanaka
(Continued)

FOREIGN PATENT DOCUMENTS

EP 2453444 5/2012
JP S6444899 2/1989
WO WO2005053794 6/2005

OTHER PUBLICATIONS

Patent Cooperation Treaty, Int'l Search Report, dated Jun. 5, 2020; Form PCT/ISA/237.

*Primary Examiner* — Kiet T Nguyen
(74) *Attorney, Agent, or Firm* — Pitts & Lake, P.C.

(57) ABSTRACT

A system proton treatment system including a proton accelerator structured to generate a proton beam, a plurality of beamline pathways configured to direct the proton beam from the proton accelerator to a corresponding plurality of treatment rooms, a rotatable bending magnet located between the proton accelerator and the plurality of treatment rooms, the rotatable bending magnet being structured to selectively rotate between multiple treatment rooms, and an upright patient positioning mechanism disposed in each of the treatment rooms, the upright patient positioning mechanism being structured to support a patient within a particular treatment room and to rotate the patient between a fixed imaging source and imaging panel.

23 Claims, 13 Drawing Sheets

(52) U.S. Cl.
CPC ......... *A61N 5/1077* (2013.01); *A61N 5/1081* (2013.01); *A61N 5/1082* (2013.01); *A61N 2005/1057* (2013.01); *A61N 2005/1062* (2013.01); *A61N 2005/1087* (2013.01); *A61N 2005/1094* (2013.01)

(58) Field of Classification Search
CPC ................ A61N 5/1077; A61N 5/1082; A61N 2005/1094; A61N 2005/1087; A61N 2005/1097; A61N 2005/105; A61N 2005/1052; A61N 2005/1061; A61N 2005/1059; A61N 2005/1057; A61N 2005/1062
USPC ...................................................... 250/492.3
See application file for complete search history.

(56) References Cited

U.S. PATENT DOCUMENTS

| | | |
|---|---|---|
| 5,818,058 A | 10/1998 | Nakanishi et al. |
| 6,683,318 B1 | 1/2004 | Haberer et al. |
| 7,728,311 B2 | 6/2010 | Gall |
| 7,953,205 B2 | 5/2011 | Balakin |
| 8,373,143 B2 | 2/2013 | Balakin |
| 8,963,112 B1 | 2/2015 | Balakin |
| 9,711,254 B2 | 7/2017 | Bromberg |
| 2007/0131876 A1 | 6/2007 | Brahme |
| 2008/0217561 A1 | 9/2008 | Mackie et al. |
| 2011/0101236 A1 | 5/2011 | Cameron et al. |
| 2011/0284757 A1 | 11/2011 | Butuceanu et al. |
| 2013/0066134 A1 | 3/2013 | Carol |
| 2014/0239198 A1 | 8/2014 | Ein-Gal |
| 2017/0036041 A1* | 2/2017 | Reichert ................ A61B 6/032 |
| 2017/0106213 A1* | 4/2017 | Lee ........................ A61B 6/032 |
| 2017/0259084 A1* | 9/2017 | Bennett ................ A61N 5/1049 |
| 2018/0256919 A1 | 9/2018 | Shen |

\* cited by examiner

US 11,369,807 B2

COMPACT PROTON THERAPY SYSTEMS AND METHODS

CROSS-REFERENCE TO RELATED APPLICATIONS

This application claims priority from U.S. Provisional Patent Application Ser. No. 62/790,856, filed on Jan. 10, 2019, which is incorporated herein in its entirety by reference.

FIELD OF INVENTION

The present general inventive concept relates to proton therapy systems, and, more particularly, to compact beamline proton therapy systems with improved patient positioning, proton delivery, and imaging.

BACKGROUND

Proton Therapy (PT) is a cancer treatment technology that uses high energy protons to penetrate a patient's body and deposit energy into treatment areas such as cancerous tumors. Conventional PT systems typically implement a rotating gantry wheel that directs the proton beam to the patient from any angle between zero and 360 degrees. This allows the physician to design a treatment plan that attacks cancerous tumors from different angles and reduces radiation damage to critical organs and/or healthy tissue. However, one of the challenges facing current proton therapy is the high cost and size requirements for such systems, which inhibits this effective type of therapy from becoming widely used and accepted. As such, it would be desirable to provide a proton therapy system that is able to be more compactly implemented to reduce project and equipment costs.

BRIEF SUMMARY

According to various example embodiments of the present general inventive concept, novel aspects of proton therapy systems described herein can provide improved patient fixation and positional systems as well as compact beamline delivery, advanced imaging, and improved workflow.

Additional features and embodiments of the present general inventive concept will be set forth in part in the description which follows, and, in part, will be obvious from the description, or may be learned by practice of the present general inventive concept.

The foregoing and/or other aspects and advantages of the present general inventive concept may be achieved by providing a proton treatment system including a proton accelerator structured to generate a proton beam, a plurality of beamline pathways configured to direct the proton beam from the proton accelerator to a corresponding plurality of treatment rooms, a rotatable bending magnet located between the proton accelerator and the plurality of treatment rooms, the rotatable bending magnet being structured to selectively rotate between a first position and a second position such that when the rotatable bending magnet is rotated to the first position, the rotatable bending magnet directs the proton beam to a first treatment room, and when the rotatable bending magnet is rotated to the second position, the rotatable bending magnet directs the proton beam to a second treatment room, a plurality of proton delivery nozzles located downstream of the rotatable bending magnet within each treatment room and structured to direct the proton beam to a fixed location within each treatment room, respectively, and an upright patient positioning mechanism disposed in each of the treatment rooms, the upright patient positioning mechanism being structured to support a patient within a particular treatment room such that the fixed location of the particular treatment room is located at an isocenter of a target area of the patient when the proton beam is delivered to the particular treatment room.

The foregoing and/or other aspects and advantages of the present general inventive concept may also be achieved by providing a rotating bending magnet assembly for use in a proton treatment system, including an achromatic superconducting magnet configured to change the direction of a proton beam by approximately 90 degrees, and a movement mechanism structured to rotate the achromatic superconducting magnet so as to selectively direct the proton beam in a first direction or a second direction, where the first direction is opposite to the second direction.

The foregoing and/or other aspects and advantages of the present general inventive concept may also be achieved by providing a proton treatment system including a proton accelerator structured to generate a proton beam, a plurality of beamline pathways configured to direct the proton beam from the proton accelerator to a corresponding plurality of treatment rooms, a rotatable bending magnet located between the proton accelerator and the plurality of treatment rooms, the rotatable bending magnet being structured to selectively rotate between a first position and a second position such that when the rotatable bending magnet is rotated to the first position, the rotatable bending magnet directs the proton beam to a first treatment room, and when the rotatable bending magnet is rotated to the second position, the rotatable bending magnet directs the proton beam to a second treatment room, and a plurality of proton delivery nozzles located downstream of the rotatable bending magnet within each treatment room and structured to direct the proton beam to a fixed location within each treatment room, respectively.

The foregoing and/or other aspects and advantages of the present general inventive concept may also be achieved by providing an upright positioning mechanism to be used with a proton treatment system, the upright positioning mechanism including a base member structured to rotate about an isocenter of a target area of a patient, and a patient support post structured to extend upward from the base member, and to be pivotable with respect to the base member, wherein the upright patient positioning mechanism is structured to support the patient and provide six degrees of freedom in movement within a treatment room such that a fixed line proton beam is delivered to the isocenter of the target area of the patient.

The foregoing and/or other aspects and advantages of the present general inventive concept may also be achieved by providing a method of performing three-dimensional image reconstruction during proton treatment of a patient, the method including rotating a patient between a fixed imaging source and imaging panel, generating a series of images of a target area of the patient, and reconstructing the images into three-dimensional volumetric representations.

Other features and embodiments may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Figure 1:
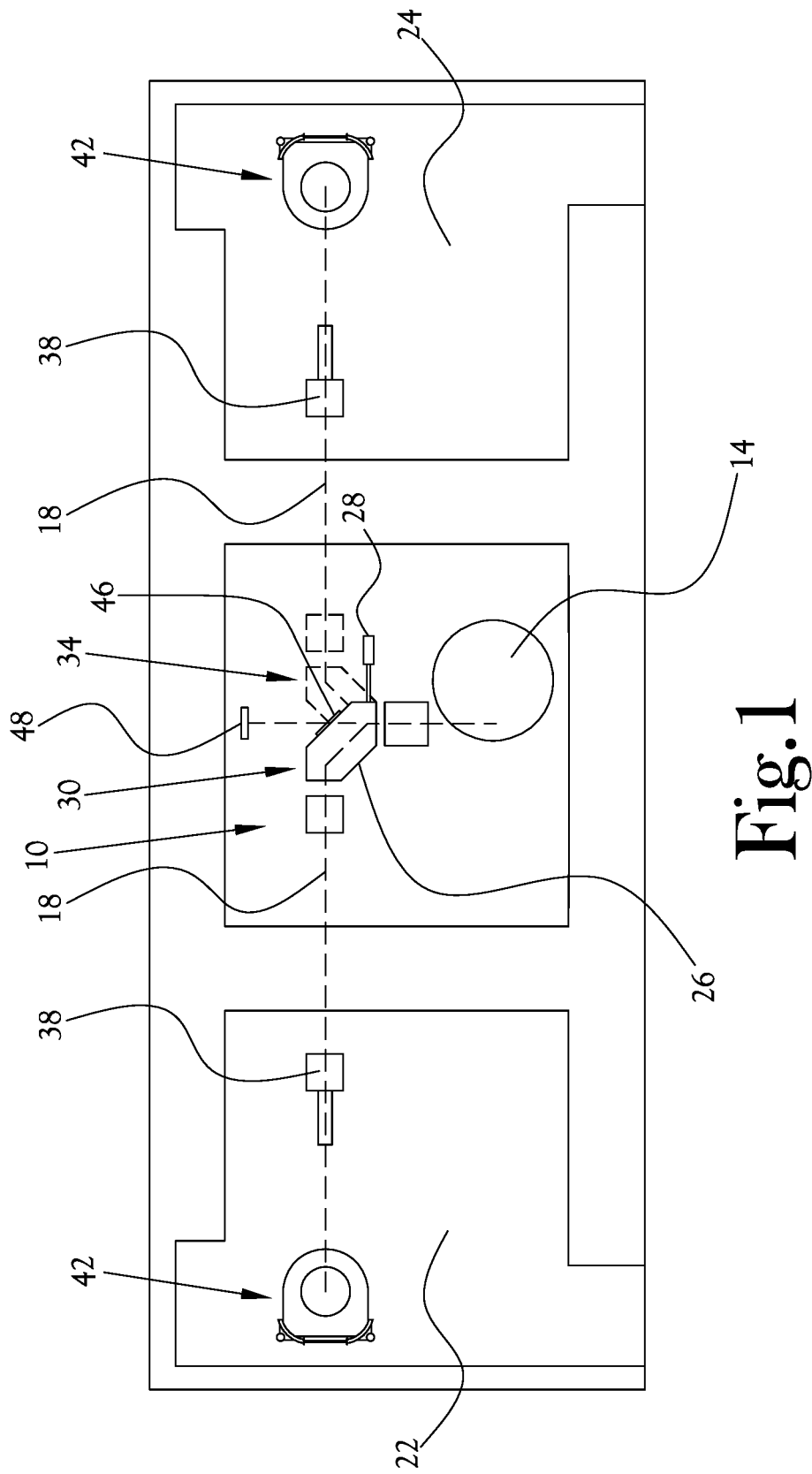
FIG. 1 illustrates a proton treatment system according to an example embodiment of the present general inventive concept.

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be simplified and/or omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Various example embodiments of the present general inventive concept may significantly reduce project and equipment costs by providing a compact superconducting accelerator and fixed beamline with upright patient treatment. Such embodiments may reduce building footprints, improve clinical accuracy, and reduce equipment costs.

According to various example embodiments of the present general inventive concept, a compact superconducting cyclotron and a 90 degree bending magnet can be configured to replace the long beamlines of current systems. 90 degree (right angle) delivery permits the beamline to be directed into one or more treatment rooms by rotating the bending magnet between multiple fixed beamlines "downstream" from the cyclotron and bending magnet. For example, a 90 degree rotating bending magnet can be configured to selectively direct a horizontally oriented beamline to two available treatment rooms (e.g., room 1 or room 2). In various example embodiments it is also possible to orient the beam generator to generate a vertical beamline into a room such that the 90 degree bending magnet can be configured to bend the beamline into a horizontal orientation and selectively direct the beamline into one of a plurality of treatment rooms (e.g., a hub and spoke configuration).

Various example embodiments of the present general inventive concept may also provide patient positioning systems that are configured to support the patient in an upright position and move the patient in relation to the proton beam, rather than rotating a beamline around the patient with a gantry system. Upright treatment significantly improves the number of fractions that can be treated per hour, simplifies imaging, and reduces the footprint of the treatment room. The patient can be placed upright in, for example, a seated or perched position, and rotated about the isocenter. Additionally, such accurate rotation permits 3D CBCT images to be developed by rotating the patient and not the imager. Imaging panels and sources can be fixed in space, improving accuracy and drastically reducing cost, as well as simplifying the positioning mechanisms. It has been shown that treating a patient in the same position as the patient was scanned can be advantageous due to displacement of organs when the patient is moved from a lying to an upright position. The advantages of treating the patient in a seated or upright position have been systematically addressed by several scholars in the field. It has been shown that treating patients in a seated or upright position can result in improved patient comfort and safety, less target motion, and less lung volumes being irradiated. Example embodiments of the present general inventive concept may provide planning systems configured to accommodate visualization of an upright patient. Software functionality can be coordinated with the development of the proton equipment for processing efficiency.

The 90 degree bending magnet provided in various example embodiments of the present general inventive concept may be used to form a compact proton therapy system to facility a small footprint for the system, allowing the corresponding buildings and lots to be constructed of perpendicular construction elements. A compact right-angle bend can be placed immediately adjacent to walls and structural elements without unnecessary space used for the sweep of the bends along the length of the beamline. A rotating 90 degree bending magnet can be extended to more than 2 treatment rooms or treatment locations. For example, in a hub and spoke configuration, the cyclotron can be pointed upward, or downward, and the bending magnet can place the beam into a horizontal plane and rotate delivery of the beam into a plurality of rooms arranged in a radial fashion about the bending magnet.

Figure 11:
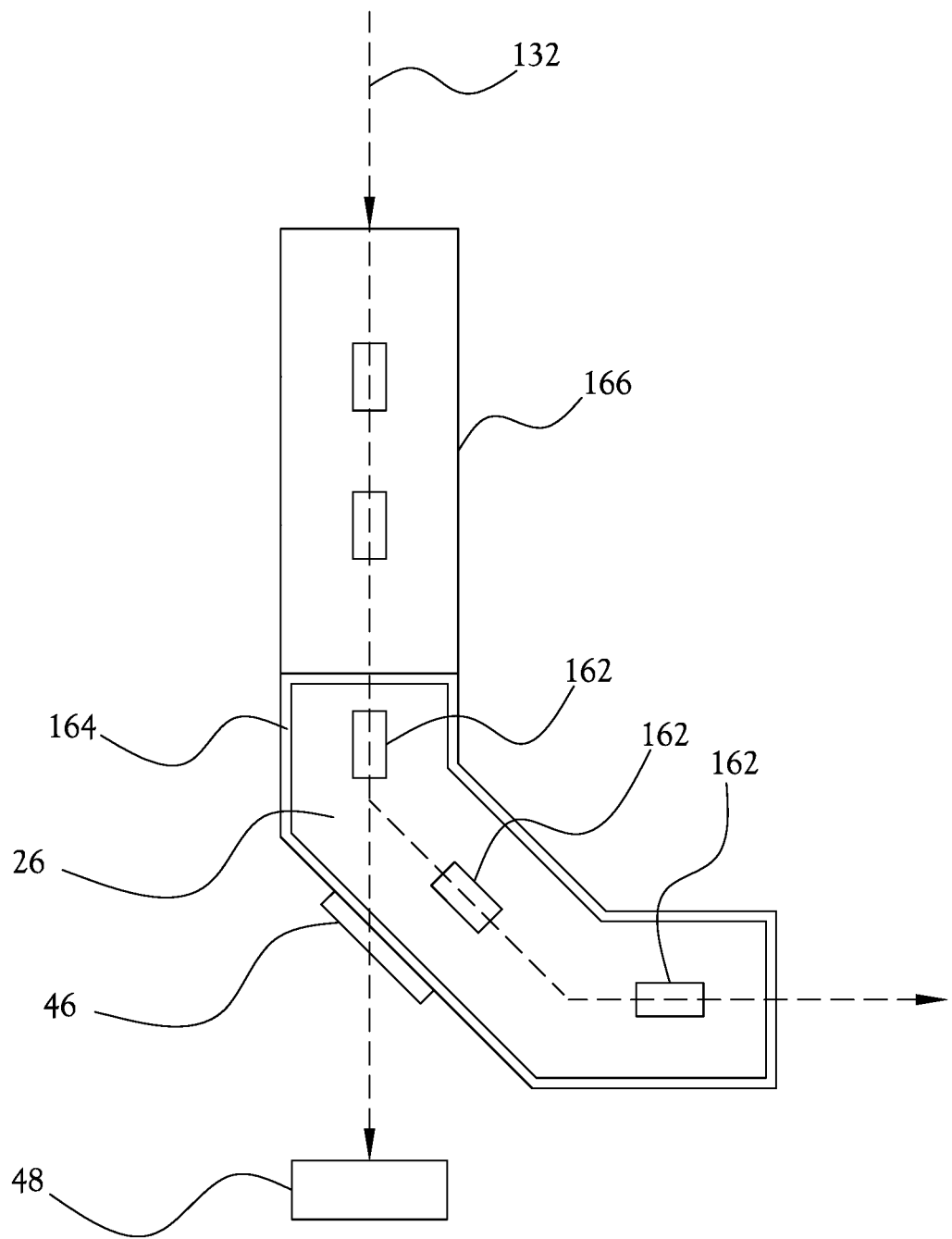
FIG. 11 illustrates a rotatable bending magnet with a common housing according to an example embodiment of the present general inventive concept.

FIG. 1 illustrates a proton treatment system according to an example embodiment of the present general inventive concept. As illustrated in FIG. 1, the proton treatment system 10 of this example embodiment includes a proton accelerator 14 configured to generate a proton beam to be used in the proton treatment, and a plurality of beamline pathways 18 arranged to direct the proton beam from the proton accelerator 14 to a corresponding plurality of treatment rooms. In this example embodiment, two beamline pathways 18 are arranged to deliver the proton beam to respective first and second treatment rooms 22,24. A rotatable bending magnet 26 is provided between the accelerator 14 and treatment rooms 22,24 to bend the proton beam from the proton accelerator 14 ninety degrees so as to route the proton beam to a selected one of the beamline pathways 18 for delivery to the selected one of the treatment rooms 22,24. The rotatable bending magnet 26 is structured to selectively rotate between a first position 30 and a second position 34 such that when the rotatable bending magnet 26 is rotated to the first position 30, the rotatable bending magnet 26 directs the proton beam to the first treatment room 22, and when the rotatable bending magnet 26 is rotated to the second position 34, the rotatable bending magnet 26 directs the proton beam to the second treatment room 24. A movement mechanism 28 can be provided to rotate the rotatable bending magnet 26 for switching between treatment rooms. The movement mechanism 28 can also be configured to rotate the bending magnet 26 to a different angle, for example directly downward or upward, to direct the proton beam to a diagnostic unit 48 for analysis of the proton beam before the proton beam is delivered to the treatment room. After the proton beam is analyzed, the movement mechanism 28 can then rotate the bending magnet 26 to direct the proton beam into one of the treatment rooms for delivery to the patient. Various known or later developed mechanical or electro-mechanical structures can be utilized for the movement mechanism 28 according to sound engineering judgement. For example, a gear driven ring-like structure can be mounted to the bending magnet to facilitate rotation of the bending magnet. The movement mechanism 28 can be controlled by an electronic servo-mechanism to drive the gear-driven structure and rotate the bending magnet 26 between treatment rooms or to direct the proton beam to the diagnostic unit 48. A plurality of proton delivery nozzles 38 are provided downstream of the rotatable bending magnet 26, within each of the respective treatment rooms 22,24, to direct the proton beam to a fixed location within each of the treatment rooms 22,24. An upright patient positioning mechanism 42 is disposed in each of the treatment rooms 22,24, the upright patient positioning mechanism 42 being configured to support a patient within a particular treatment room such that the fixed location of the particular treatment room is located at an isocenter of a target area of the patient when the proton beam is delivered to the particular treatment room. Various example embodiments of the upright patient positioning mechanism 42 will be described in greater detail herein. As shown in FIG. 1, proton therapy systems according to various example embodiments of the present general inventive concept may be implemented in smaller and simpler building layouts, and the proton beam may be conveniently and quickly routed between different treatments rooms. As such, treatment efficiency may be increase by treating a first patient in the first treatment room 22 while a second patient is being positioned for treatment in the second treatment room 24, and switching the proton beam to the second treatment room 24 to treat the second patient immediately the first patient's treatment is completed, and so on. In various example embodiments, the rotatable bending magnet 26 is configured to be housed in a common housing to improve stability and performance of the rotatable bending magnet 26. Such a common housing can be considered as providing a "beamline in a box," and provides such benefits as saving time spent adjusting and maintaining alignment, rigid rotatable bending magnet support, lower power consumption, reduced footprint, etc. Various structures can be utilized for the common housing according to sound engineering judgement. Example structures are illustrated and described in the Applicants' U.S. Pat. No. 9,283,408, the contents of which are incorporated by reference herein in its entirety. In these drawings, the beamline pathways 18 typically refer to the portion of beamline pathways downstream of the rotatable bending magnet 26. As illustrated in FIG. 1, rather than rotating the bending magnet 26 to direct the proton beam to the diagnostic unit 48, it is also possible to provide the rotatable bending magnet 26 with an access window 46 that may be selectively activated to allow the proton beam to selectively pass through the access window 46 of the rotatable bending magnet 26 without changing a direction of the proton beam when the bending magnet is otherwise positioned to direct the proton beam into one of the treatment rooms. When the access window 46 is activated, the proton beam can be delivered to a diagnostic unit 48 configured to measure one or more characteristics of the proton beam passing through the access window 46. Thus, the proton beam can be passed to the diagnostic unit 48 instead of into one of the treatment rooms 22,24, so that various characteristics of the proton beam may be analyzed before the proton beam is directed to the patients. Various different diagnostic units or componentry may be interchangeable at a convenient location proximate the access window 46 without disrupting procedures and/or arrangements in the treatment rooms. In various example embodiments the optional access window 46 may be structured in a host of different ways, such as a selectively opening panel, selectively actuated windows or apertures, and so on. For example, as illustrated in FIG. 11, one or more beam-steering electromagnets 162 within a common housing 164 of the rotatable bending magnet 26 can be selectively energized to direct the proton beam 132 through the access window 46 rather than into one of the treatment rooms.

Figure 2:
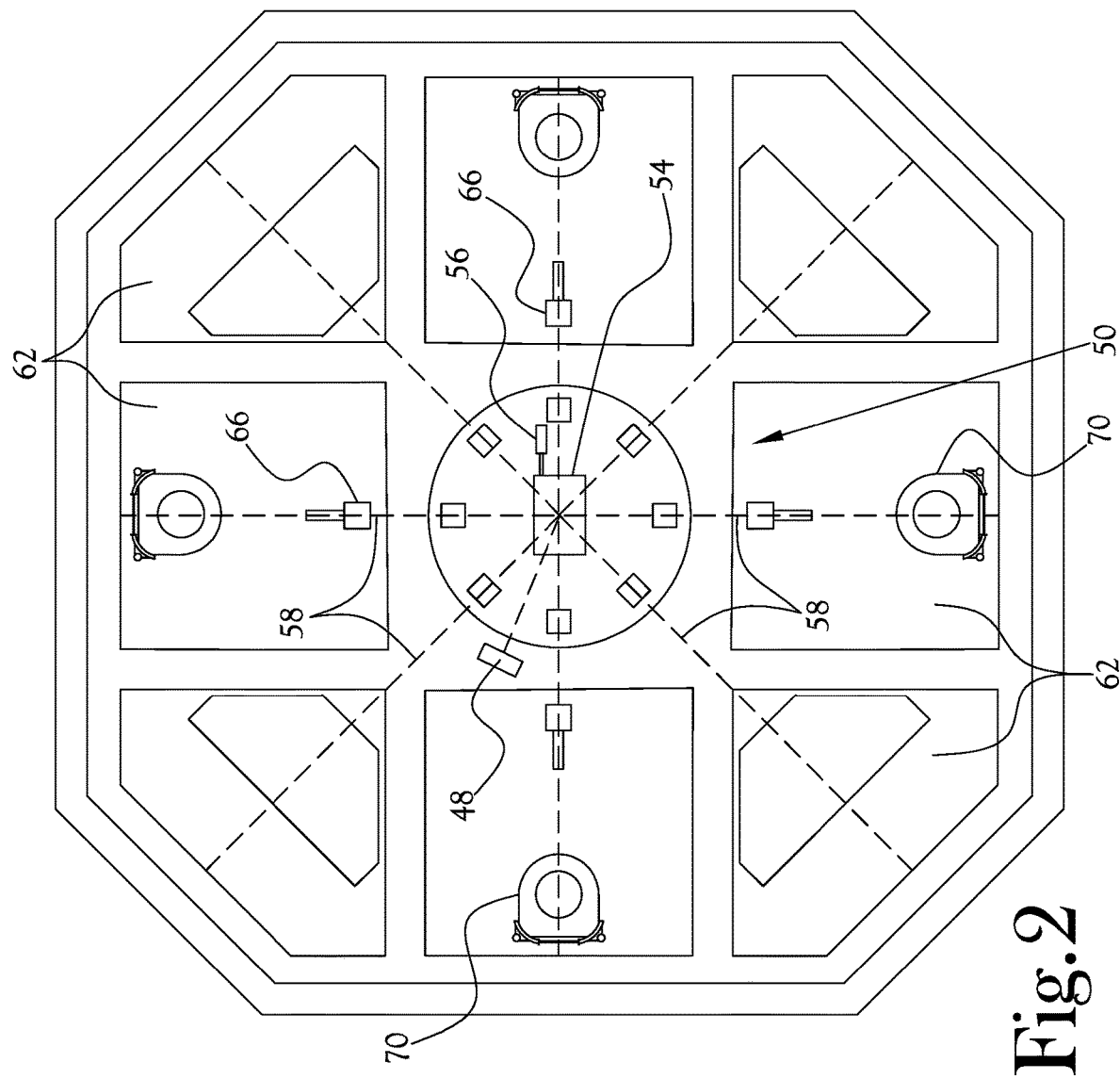
FIG. 2 illustrates a proton treatment system according to another example embodiment of the present general inventive concept.

In the example embodiment illustrated in FIG. 1, the proton is accelerator 14 is configured to direct the proton beam in a substantially horizontal plane relative to the floor of the first and second treatment rooms 22,24, and the rotatable bending magnet 26 is structured to be selectively rotatable between the first and second positions 30,34 to bend the proton beam approximately 90 degrees on the substantially horizontal plane to selectively direct the proton beam into one of the first and second treatment rooms 22,24. However, various example embodiments may provide a host of different configurations. For example, FIG. 2 illustrates a proton treatment system according to another example embodiment of the present general inventive concept, in which the proton therapy system 50 is arranged in a hub and spoke configuration such that a rotatable bending magnet 54 bends the proton beam 90 degrees and perpendicular to the direction of the proton beam delivered by the proton accelerator (not shown in this drawing). The proton accelerator is configured to direct the proton beam in a substantially vertical direction with respect to the floor of a plurality of treatment rooms 62 arranged about the rotatable bending magnet 54, which is structured to bend the proton beam approximately 90 degrees with respect to the vertical direction so as to direct the proton beam to a selected one of the plurality of treatment rooms 62. In such a configuration the rotatable bending magnet 54 can include a movement mechanism 56 (for example similar to movement mechanism 28 described above) configured to rotate the rotatable bending magnet 54 in desired increments up to 360 degrees, enabling the rotatable bending magnet 54 to direct the proton beam into any number of treatment rooms arranged about the rotatable bending magnet 54 and/or to the diagnostic unit 48. In the example embodiment illustrated in FIG. 2, the rotatable bending magnet 54 is configured to be rotatable between multiple positions, but it is noted that the present general inventive concept is not limited to any particular number of rooms and/or directional (angular) orientations. Here, the movement mechanism 56 can be provided to the rotatable bending magnet 54 for switching between any one of the treatment rooms and/or optionally to the diagnostic unit. Various known or later developed mechanical or electro-mechanical structures can be utilized to carry out the incremental rotation of the rotatable bending magnet 54 according to sound engineering judgement. In some embodiments, the movement mechanism 56 can be a gear driven ring-like structure mounted to the bending magnet 54 to facilitate rotation of the bending magnet 54. The movement mechanism 28 can be controlled by an electronic servo-mechanism to drive the gear-driven structure and rotate the bending magnet 54 to any one of treatment rooms 62 and/or to direct the proton beam to the diagnostic unit 48. While the proton accelerator is not illustrated in this FIG. 2, it may be provided at a position below or above the rotatable bending magnet 54 to direct the proton beam vertically to the rotatable bending magnet 54. In the example embodiment illustrated in FIG. 2, the rotatable bending magnet 54 is configured to be selectively rotatable to deliver the proton beam in eight different directions along eight different beamlines 58 to eight respective treatment rooms 62. Four of the treatment rooms 62 are provided with respective proton beam delivery nozzles 66 and upright patient positioning mechanisms 70, but it is understood that a host of different configurations may be implemented without departing from the scope of the present general inventive concept.

Figure 3:
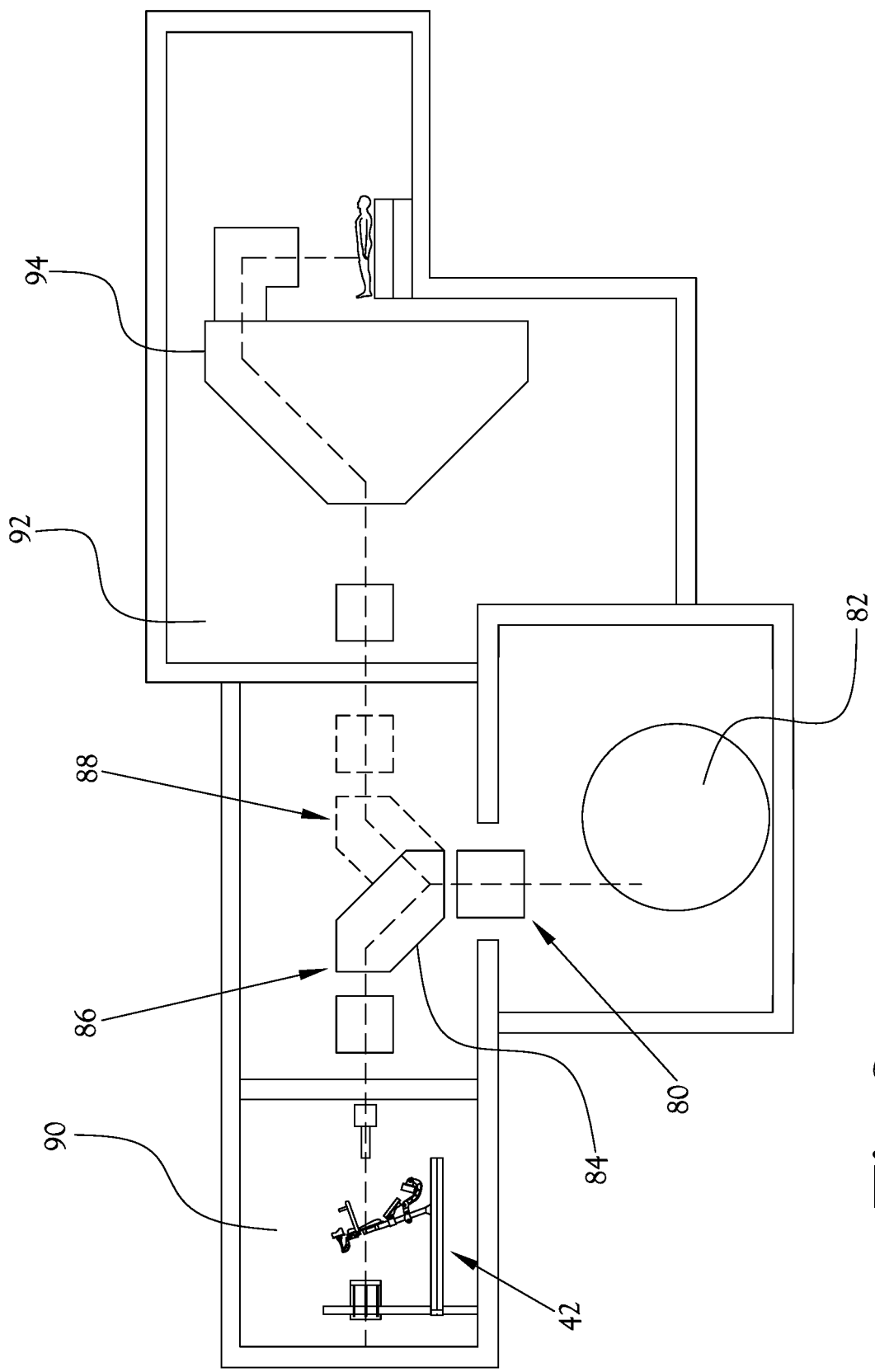
FIG. 3 illustrates a proton treatment system according to yet another example embodiment of the present general inventive concept.

FIG. 3 illustrates a proton treatment system according to yet another example embodiment of the present general inventive concept. In the example proton treatment system 80 illustrated in FIG. 3, a proton accelerator 82 is arranged below a rotatable bending magnet 84 that is configured to be selectively rotatable between a first position 86 and a second position 88. When the rotatable bending magnet 84 is in the first position 86 the proton beam from the proton accelerator 82 is delivered to a first treatment room 90 in which an upright patient positioning mechanism 42 is disposed, and when the rotatable bending magnet 84 is rotated to the second position 88 the proton beam from the proton accelerator 82 is delivered to a second treatment room 92 in which a gantry type proton therapy assembly 94 is provided. Thus, in various example embodiments of the present general inventive concept the rotatable bending magnet 84 may be utilized to selectively deliver a proton beam to rooms with gantry systems 94, to which at least portions the proton treatment system 80 may have been retrofitted, or to a treatment room with an upright patient positioning mechanism or assembly as described herein. It is noted that the proton accelerator 82 is illustrated as being located below the rotatable bending magnet 84 merely as an example configuration, and could also be located above the rotatable bending magnet 84, or to a side of the rotatable bending magnet such that the proton beam is delivered to the rotatable bending magnet 84 on a substantially horizontal plane.

Various example embodiments of the present general inventive concept may provide an upright patient positioning assembly, mechanism, or system that allows a patient to be positioned and rotated such that the patient is rotated around the isocenter of the treatment target area of the patient while a proton beam nozzle is fixed, as opposed to the conventional rotation of the proton beam nozzle around the patient. Additionally, as the proton beam nozzle is fixed and the treatment target are maintained at a certain position, various imaging components may also be provided at fixed locations or deployed to fixed locations to provide convenient imaging of the target area of the patient, as well as of various properties of the proton beam. Various example embodiments of the present general inventive concept provide an array of image forming components or devices which allow for three-dimensional (3D) volumetric imaging. Rotating the patient to accomplish three-dimensional volumes can be advantageous when compared to the conventional practices of rotating the source and collector around a stationary patient, thus solving one of the primary challenges in external beam therapy, which is maintaining clearances around the patient before, during, and after treatment. Heretofore, lack of space around the patient has inhibited adoption and development of improved imaging techniques. By rotating the patient, a single automated component can replace the function of prior imagers and gantry.

Example embodiments of the upright patient positioning mechanism can be configured as a mechanical apparatus used to support a patient in a variety of desired positions during his/her treatment. The positioning mechanism may be configured to translate on the horizontal plane and along the vertical axis so that the region being treated is centered on isocenter. The positioner has a compact footprint due to the upright patient treatment and rotation about the axis of the patient. The positioner can include a platform cantilevered from a pair of vertical columns which also hold the imaging panels. The entire platform can be configured to move along the column when translating vertically, and the positioner can include a vertical post to which the patient support and fixation device attaches extending from the center of the platform.

Figure 4:
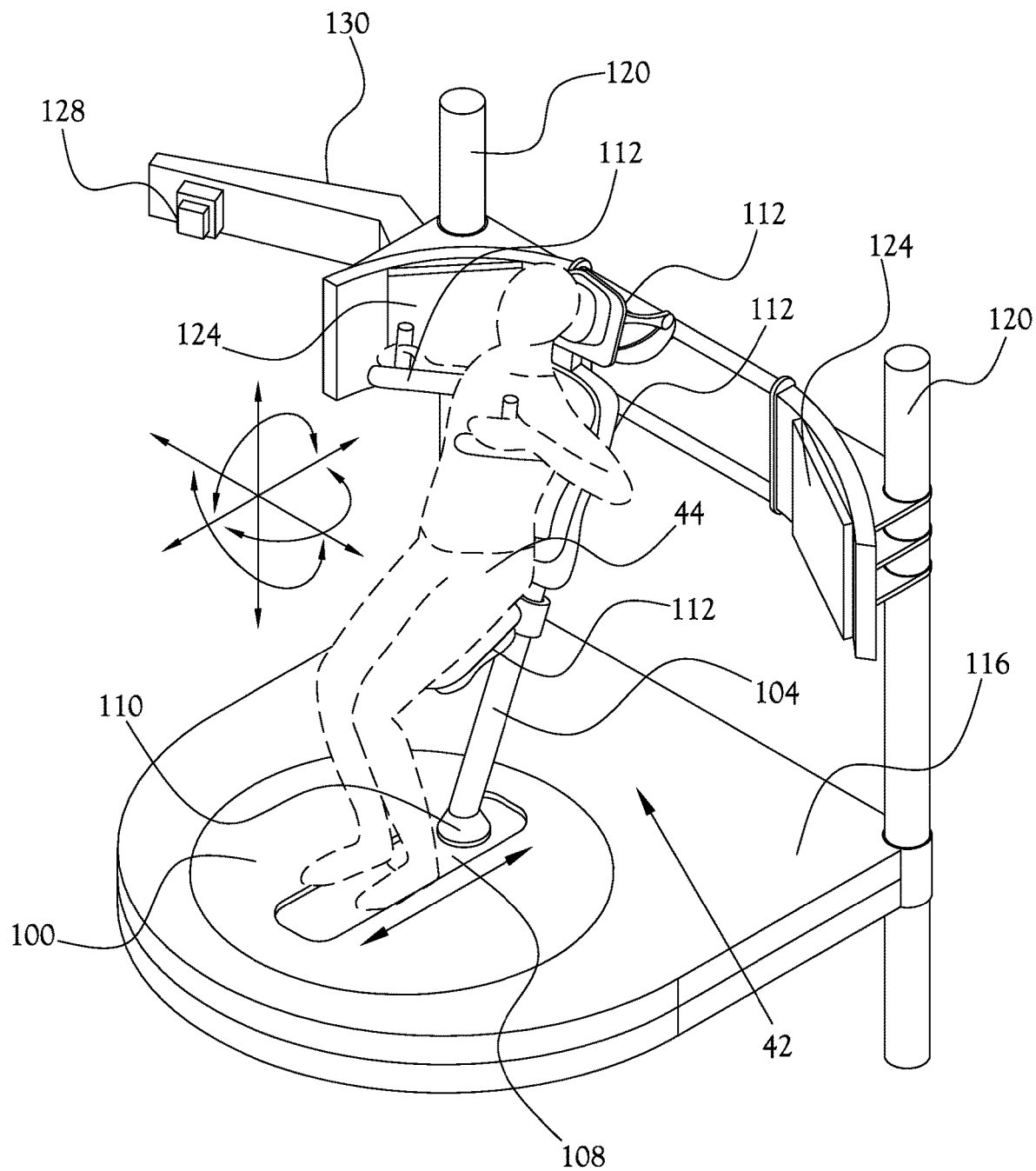
FIG. 4 illustrates an upright patient positioning mechanism according to an example embodiment of the present general inventive concept.

FIG. 4 illustrates an upright patient positioning mechanism according to an example embodiment of the present general inventive concept. The upright patient positioning mechanism 42 illustrated in FIG. 4 includes a base member 100 configured to rotate about the isocenter of a treatment target area of the patient 44. In this way, once the patient is arranged so as to be supported such that the isocenter of the target area is centered on the beamline from the fixed nozzle and a rotational axis of the base member 100, the base member 100 can be rotated such that the target area can be treated from a number of different directions (degrees of rotation) relative to the patient while the nozzle and imaging components can remain at the same locations. The upright patient positioning mechanism 42 includes a patient support post 104 structured to extend upward above the base member 100, and to be pivotable with respect to the base member 100. Thus, the patient support post 104 can pivot in a number of directions at a point proximate the base member 100 to allow the patient 44 to be supported in a position that is comfortable to the patient 44 and which has the target area properly aligned with the proton beam nozzle and associated imaging componentry. The positioning mechanism 42 includes a sliding member 108 configured on the base member 100 and structured to be reciprocally slidable or movable with respect to the base member 100. The upright patient support post 104 is coupled to the sliding member 108, and thus the bae of the patient support post 104 may be positionable at a desired point along the range of motion of the sliding member 108. The sliding member 108 may be provided with a coupling member 110 to which a bottom of the patient support post 104 is coupled, the patient support post thus being pivotable relative to the base member 100 at the desired point along the range of motion of the sliding member 108. The upright patient support post 104 is structured such that a host of various support members 112, or patient fixation accessories, may be attached to the support post 104 to support various body parts of the patient 44. In various example embodiments the upright patient support post 104 may be formed with surface structures to aid in the coupling of the support members 112, such as holes to receive mounting posts and the like, ridges and/or notches configured to receive and secure portions of the one or more support members 112 received therein, and so on. In various example embodiments the upright patient support post 104 may be formed with a series of ridges formed along the outer surface to support the one or more support members 112 affixable to the support post 104. Such support members 112 may include seats, knee supports, arm rests, handles, headrests, and the like, or any combination thereof. In various example embodiments the upright patient support post 104 may be readily attachable and detachable to the coupling member 110 so that patient support assemblies formed on the upright patient support post may be stored and maintained for easy modular utilization for daily treatments. Such modular patient supports and posts aid in both patient treatment and the preparation for the treatments. Supporting a patient on a common post, with various attachments, can achieve a well-designed and common method of fixation between attachments to enhance workflow and system adoption. Thus, a polar coordinate patient positioner may be provided, and simple mechanisms with stages built for proton therapy have been shown to reduce room dimensions significantly. Various example embodiments of the present general inventive concept include components in a compact base that are configured to accept interchangeable end effectors, thus providing a modular patient fixation interface. Having an interchangeable interface for various end effectors gives clinical practitioners the ability to expand the body of knowledge in the proton field. With conventional systems, patient fixation and devices offer less than desirable flexibility. Systems including robotic arms with specialty couches and affixed imaging equipment inhibit design and implementation of novel patient setups.

The upright patient positioning mechanism 42 illustrated in FIG. 4 includes a movable platform 116 that is configured to support the base member 100 and to be selectively raised and lowered relative to the fixed location to which the proton beam is delivered. The movable platform 116 may be structured to provide a walking/standing surface for attendants. The movable platform 116 of the upright patient positioning mechanism 42 in FIG. 4 is movably mounted on a pair of vertical columns 120 structured to support the movable platform 116, which may be slidably mounted to move up and down along the longitudinal axis of the vertical columns 120. Various example embodiments of the present general inventive concept may provide different quantities of vertical columns or other such support structures, and a number of methods of moving the movable platform up and down may be utilized without departing from the scope of the present general inventive concept. Thus, the patient 44 is positionable by a host of movable components of the upright patient positioning mechanism 42, including the rotatable base member 100, the sliding member 108, the pivotable patient support post 104 upon which a host of support members 112 may be attached at a variety of locations, the movable platform 116, etc., such that six degrees of freedom of movement are provided so that the patient 44 is rotatable about the isocenter while maintaining the treatment target area of the patient on the proton beam from the fixed proton beam nozzle.

In various example embodiments, the movable platform 116 of the positioner 42 may be dimensioned to be about 1600 mm wide, 1800 mm long, and 330 mm in thickness. When the positioner 42 is fully lowered, the movable platform 116 may be flush with the surrounding floor. When movable platform 116 of such an embodiment is raised, telescopic covers may be provided around the base of the platform 116 to prevent access to the area under the platform 116 as well as blocking the patient and therapist's view of the mechanical underpinnings for an aesthetically pleasing look. In various example embodiments a vertical post may be provided in the center of the platform to which the patient support and fixation device may be attached, and may be approximately 300 mm long and 75 mm in diameter. It is understood that the present general inventive concept is not limited to any particular dimensions. The positioner 42 can be configured to provide six degrees of freedom allowing the patient to be moved to a position where (1) the tumor is centered on Isocenter and (2) the patient is rotated such that the beam enters at the desired angle. The drive mechanism for the vertical translation can be located at the top of the pair of vertical columns 120 and hidden above a drop ceiling. A cable system running between the platform 116 and drive mechanism can be used to transfer power to raise and lower the platform 116.

Rotation about the vertical direction (yaw) can be centered on the proton beam isocenter, and it can be configured to rotate with high precision using a bearing system. High precision rotation about the proton beam isocenter has two main benefits: (1) The proton beam and imaging equipment do not have to be moved around the patient, therefore their design can be simplified as rotational motion is not required. (2) Because the treatment volume stays centered on the proton beam isocenter, imaging between treatment fields is unnecessary. The compact design is advantageous to TROF. For example, when the positioner is completely lowered only the chair and columns can be designed to protrude from the floor. The vertical translation will utilize the columns, but mechanisms for the other DOF (horizontal translation, pitch, roll, and yaw) can be hidden under the floor level when the positioner is fully lowered. The compact PP does not have a large radius of motion like the robotic arm. The therapists will not have to be aware of a large body moving around the room. The patient positioner has a familiar look, like the chair in a salon or barber shop, as opposed to the unfamiliar industrial robotic arm in the middle of the traditional treatment room. Rotating the patient vertically eliminates the need for a large "swing" radius of the existing style of robotic patient positioners. This space saving in the treatment rooms reduces overall concrete and shielding needs.

Figure 5:
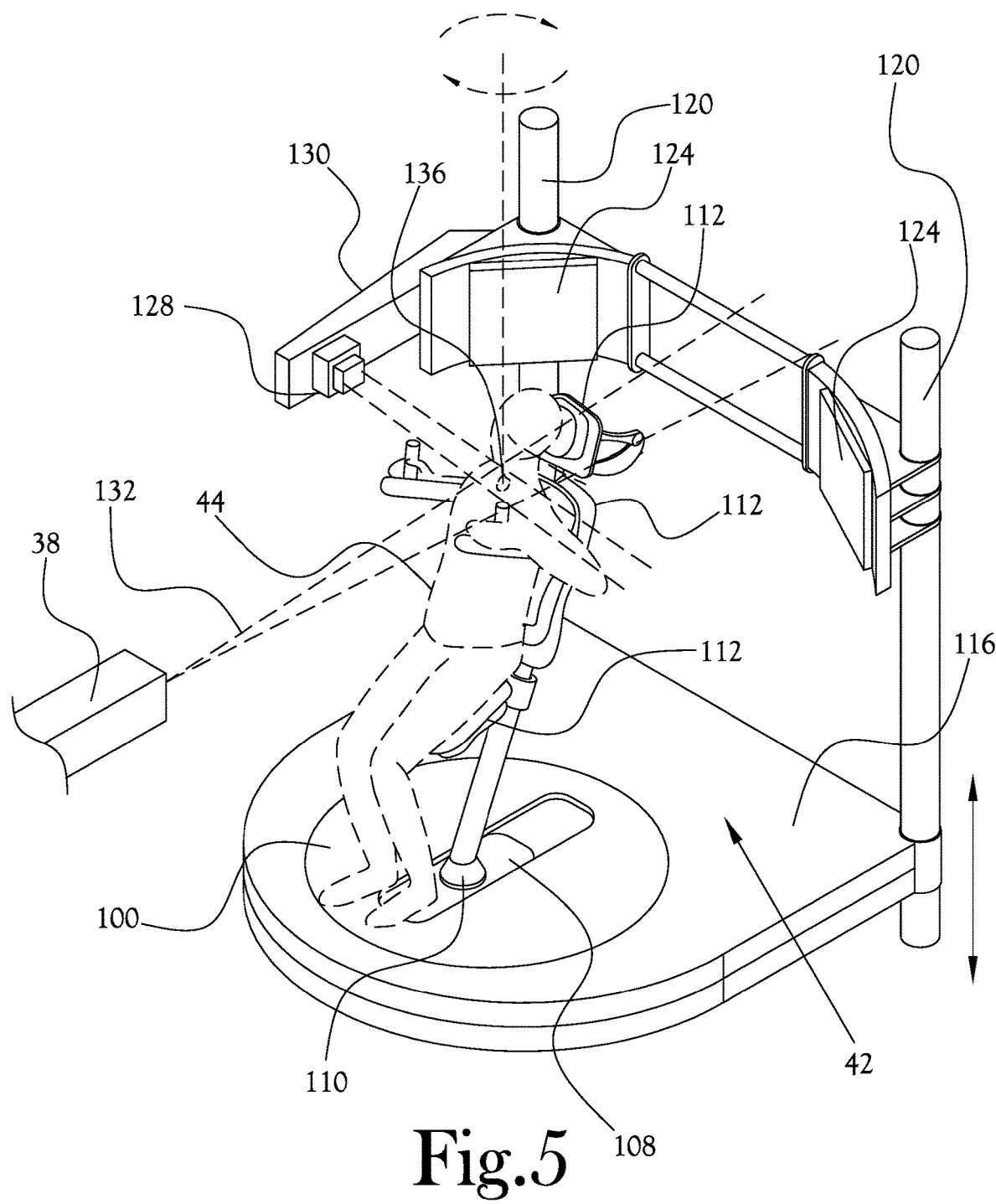
FIG. 5 illustrates the upright patient positioning mechanism of FIG. 4 in a proton therapy procedure according to an example embodiment of the present general inventive concept.

The upright patient positioning mechanism 42 of FIG. 4 includes a plurality of imaging sources (illustrated in FIGS. 7A-C and described herein) structured to scan the target area of the patient 44, and a plurality of imaging panels 124 structured to cooperate with the imaging sources to form an image of the target area. The imaging sources may be fixed to a wall in the treatment room through which the proton beam passes, or may be otherwise fixed in the room. The imaging panels 124 may be coupled to the vertical columns 120, and may be selectively moveable relative to the imaging sources, so that the imaging panels 124 may be stored in a position (a docked position) which gives clearance to the patient area during initial positioning of the patient, and then deployed at a position more proximate the patient during treatment and image scanning. As illustrated in FIG. 4 and FIG. 5, which illustrates the upright patient positioning mechanism of FIG. 4 in a proton therapy procedure according to an example embodiment of the present general inventive concept, a prompt gamma detector 128 is attached to a movable arm support 130 so as to be selectively movable to and from a deployed position proximate the patient 44 and perpendicular to the proton beam 132, centered substantially on the isocenter 136. The movable arm support 130 of this example embodiment is configured to swing into a deployed position for the prompt gamma detector 128, and swing away to provide clearance between the prompt gamma detector 128 and general patient positioning area.

Figure 6:
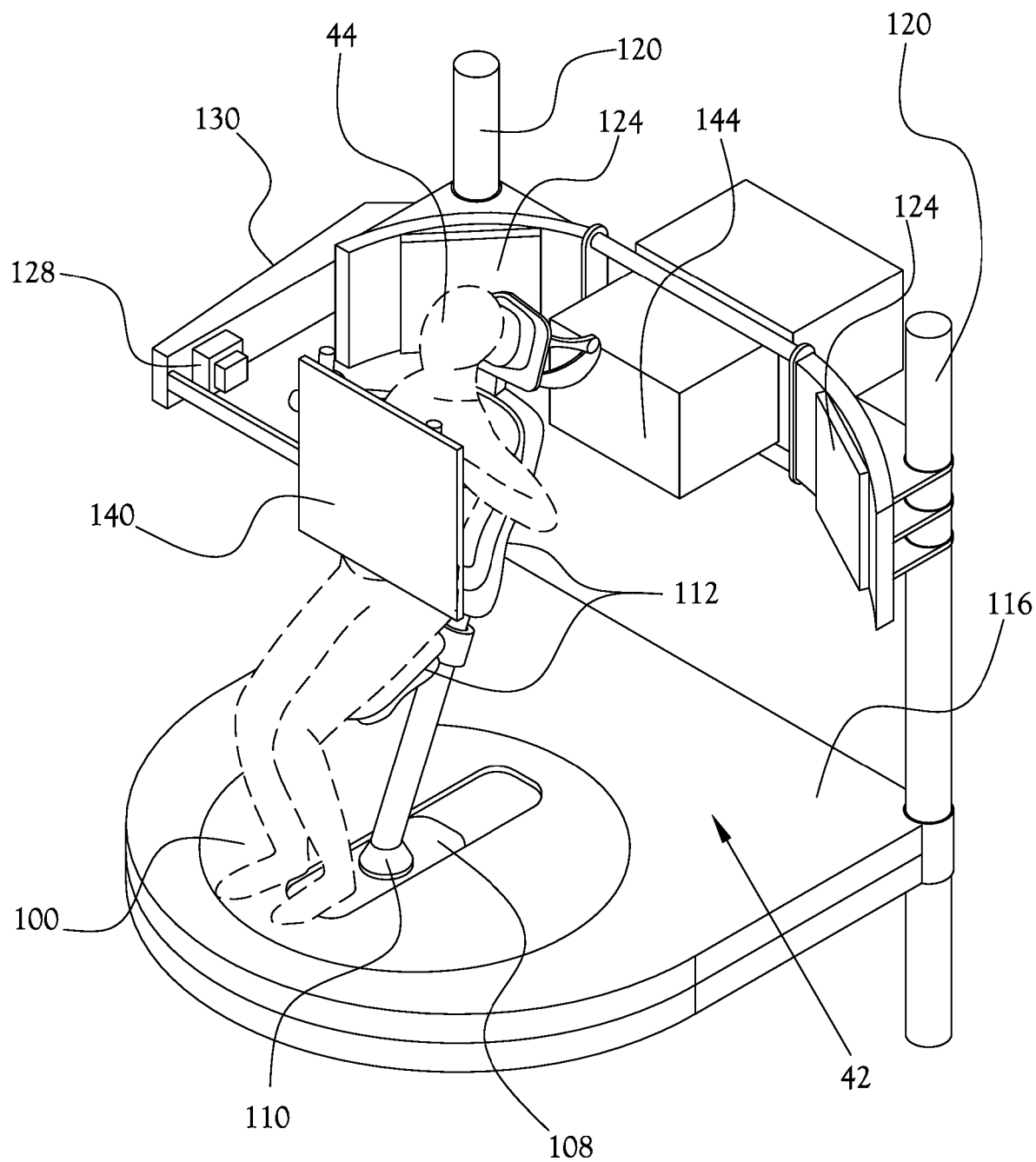
FIG. 6 illustrates the upright patient positioning mechanism of FIG. 4 configured for a proton therapy procedure according to another example embodiment of the present general inventive concept.

FIG. 6 illustrates the upright patient positioning mechanism of FIG. 4 configured for a proton therapy procedure according to another example embodiment of the present general inventive concept. As illustrated in FIG. 6, the upright patient positioning mechanism 42 is provided with a first proton radiography panel 140 that is selectively positionable upstream of the proton beam 132 relative to the patient 44, and a second proton radiography panel 144 selectively positionable downstream of the proton beam 132 relative to the patient. In various example embodiments of the present general inventive concept, one or more of the imaging panels 124, prompt gamma detector 128, and/or first and second proton radiography panels 140,144 may be connected to one or more of the plurality of vertical columns 120.

In various example embodiments of the present general inventive concept, the patient can be seated in the upright position for treatments. In some embodiments the patients can be adjusted between the seated position (head and neck) and the "perched" position for prostate and lower pelvic treatments. The upright position utilizes the constant direction of gravity and friction to maintain the patient in a comfortable position. Rotation in a seated position may need very little clearance (<1 m in some cases), whereas current patient beds typically require nearly a 2 m radius to perform movement. This "swing space" can negatively impact the overall size and cost of treatment rooms. Seated rotation can reduce the complexities and cost of a traditional gantry, while also providing the mechanism for three-dimensional volumetric imaging. For example, three-dimensional volumetric imaging can be accomplished by rotating the patient through the field of 2 x-ray sources. Rotating the patient as opposed to rotating the source and the panel can provide greater imaging stability, patient clearance and field of view. The approach permits imaging modalities such as proton radiography and prompt gamma range verification methods. To achieve enhanced workflow, it has been found that several steps once performed in series can be run in parallel to improve throughput. In various example embodiments the imaging apparatus can contain provisions for temporary or permanent attachment of range verification devices including prompt gamma detectors and proton radiography panels, ultrasound, optical tracking, surface scanning, and the like. The attachments can be modular, and therefore easily removed and attached after installation of the supporting structure. The switching magnet and compact beamline permit a very compact beamline delivery system compared to the current state of beamline design. The switching magnet can be rotating or non-rotating, including a port for the beam to enter and multiple ports for the beam to exit. Although various angular configurations can be used, it has been found that a 90 degree mechanical or electrical switching magnet is an efficient means of transferring the proton beam between patients and/or treatment rooms without a long beamline. Smaller beamlines equate to smaller building footprints and less overall project cost.

Figure 7A:
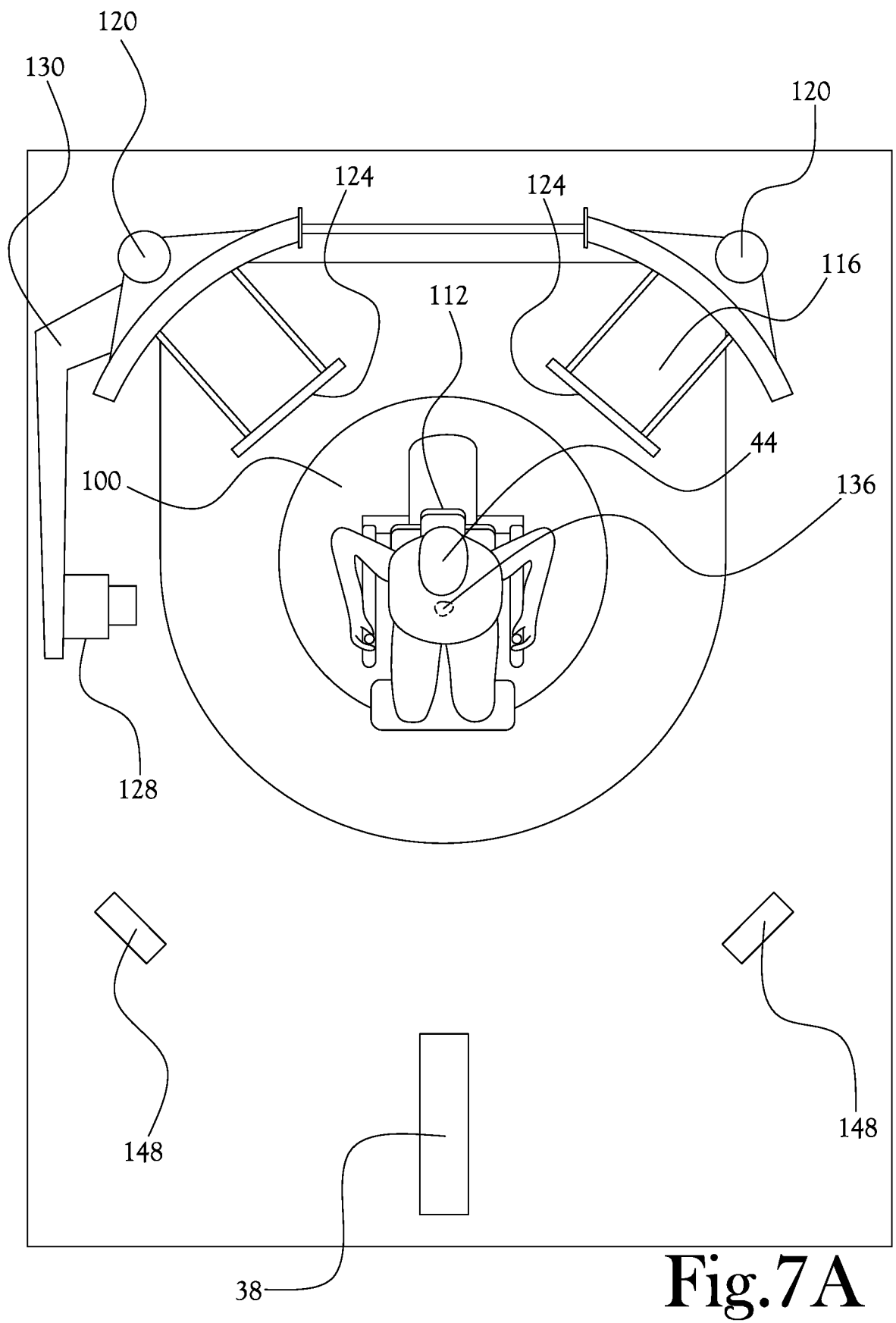
FIGS. 7A-C illustrate another view of the upright patient positioning mechanism of FIG. 4 being configured for, and being used during, a proton therapy procedure according to yet another example embodiment of the present general inventive concept.
Figure 7B:
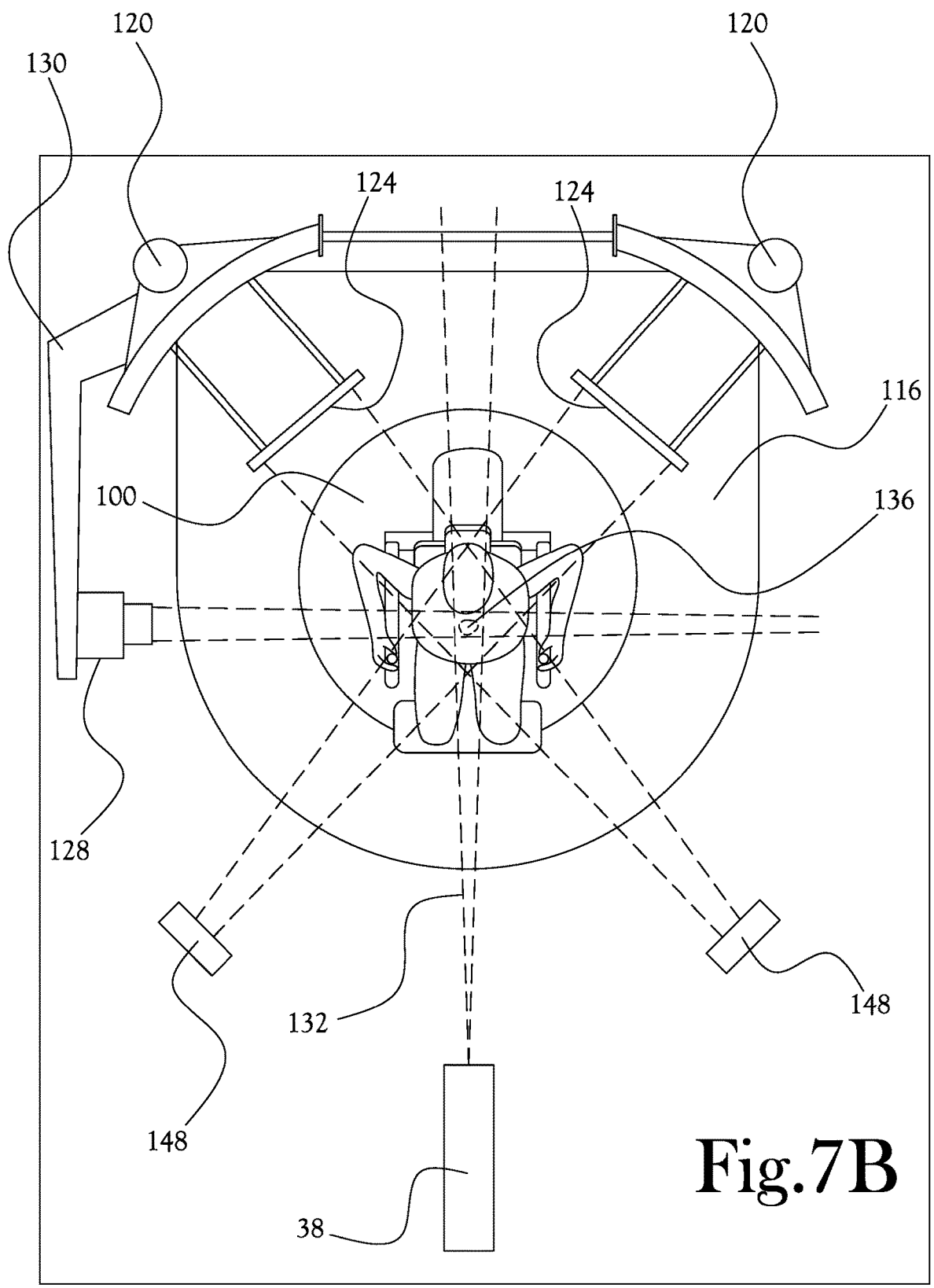
Figure 7C:
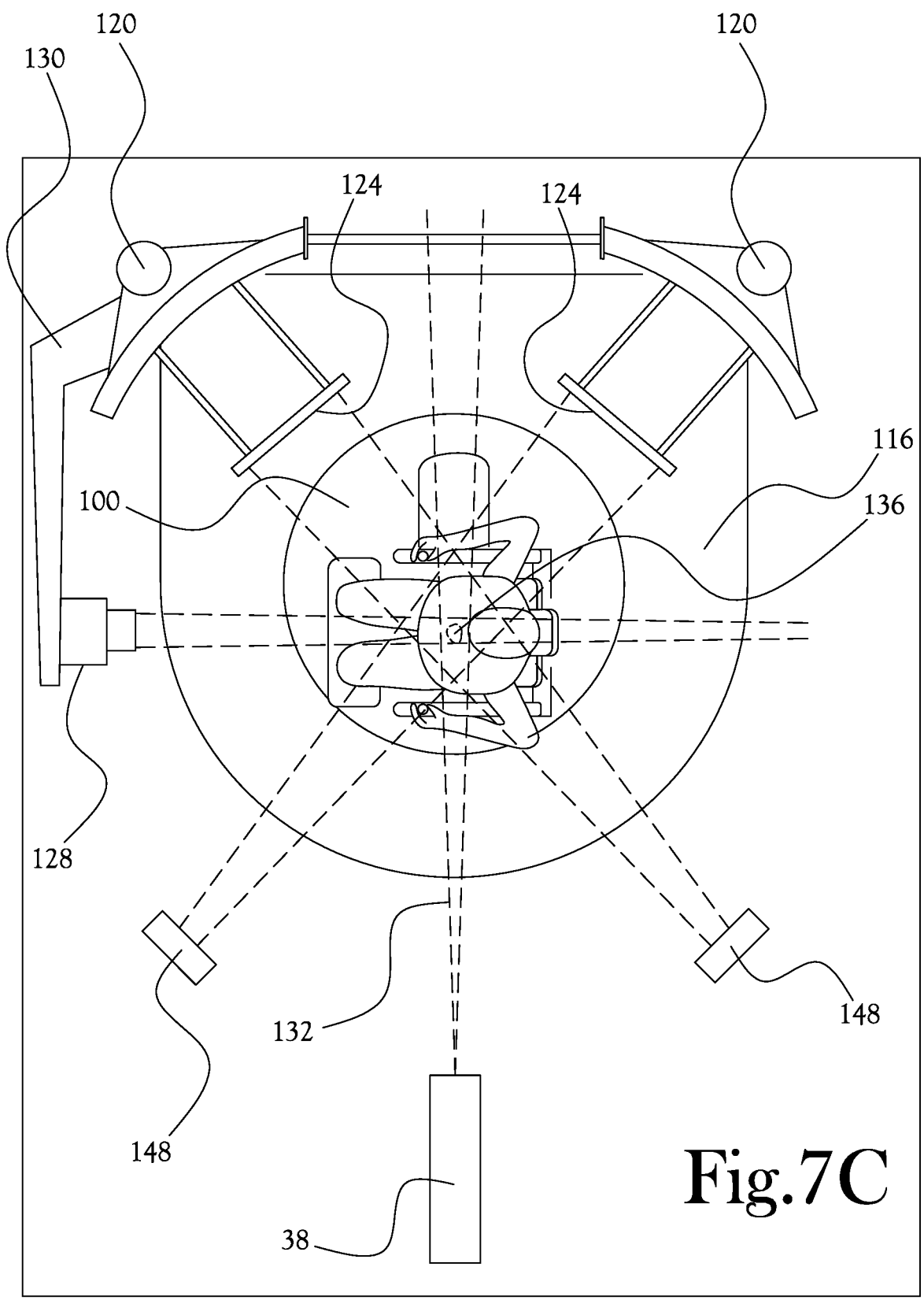

FIGS. 7A-C illustrate another view of the upright patient positioning mechanism of FIG. 4 being configured for, and being used during, a proton therapy procedure according to yet another example embodiment of the present general inventive concept. As illustrated in FIG. 7A, the base member 100, sliding member 108, moving platform 116, and various patient support members 112 have been manipulated and arranged such that the isocenter 136 is located in the desired location relative to the patient 44 and beam nozzle 38 such that the patient can be rotated about the isocenter 136 while maintaining the treatment target area in the proton beam from the fixed nozzle 38. The movable arm support 130 has been placed in position to deploy the prompt gamma detector 128, and the imaging panels 124 have been moved from their storage positions proximate the vertical columns 120 to their deployed positions in closer proximity to the patient, so as to receive, for example, x-rays, from the imaging sources 148. In FIG. 7B the proton beam 138 is being delivered to the patient, while simultaneously the imaging sources 148 are transmitting x-rays to the respective corresponding imaging panels 124 and the prompt gamma detector is operating to detect prompt gammas produced by the interaction between the proton beam and the biological tissue of the patient 44. In FIG. 7C the patient has been rotated to another position, maintaining the relative positions of target area and proton beam 132 to isocenter 136, while the treatment, imaging, and prompt gamma detection procedures are again being simultaneously performed.

As illustrated, the component designs can be configured to allow clearance for the diagnostic imager. The integrated design allows all modalities to scan the patient when positioned at or near the beam isocenter. To allow easy access to the patient, each component can independently retract into a docked position during initial patient setup then deploy when needed for imaging. As described herein, such a system can be configured to rotate the patient through one or more fixed x-ray sources and detector panels. This removes or reduces the need to perform complex geometric corrections to account for source/panel sag due to gravity, thus leading to higher accuracy and precision for the reconstructed volume.

Various example embodiments can be configured to utilize two "fixed" x-ray sources mounted on or near the treatment wall, and two panels positioned behind the patient. In such an embodiment, without rotating the patient the two source/panel pairs can be used to obtain stereoscopic radiographs for 2D/3D image registration. After rotating the patient for a CBCT acquisition, the transverse FOV diameter and maximum frontal plane FOV may be 33 cm with the panels in their standard orientation (i.e., with the X-ray cones centered on the treatment isocenter). With the panels offset to their maximum angle of 70 degrees, the FOV diameter in the transverse plane may be increased to approximately 64 cm after the patient is rotated 360 degrees about isocenter. In order direct the x-rays from the source to each of these panel positions, the system may incorporate a collimator assembly with moveable jaws.

A key feature in the imaging system of example embodiments of the present general inventive concept is that each of these imaging modalities (2D vs. 3D) and protocols (SFOV, FOV, full-scan, short-scan) can be performed with the patient in the treatment position, as opposed to other 3D imaging system which either scan the patient at a fixed location in the room with an independent scanner (i.e., diagnostic CT) or employ a couch-mounted system that can image at multiple locations in the room but typically not at the treatment position due to collisions with the nozzle as the x-ray source/panel rotates around the patient. This not only improves positioning accuracy due to reduced adjustments with the registration corrections, but also saves valuable time in the treatment workflow since the patient does not have to first be moved to a safe imaging position and then to the treatment position.

The X-ray images can display different stopping powers of Photons within the patient. The stopping power of protons is related to the stopping power of photons by means of Hounsfield units. This correlation has error (range uncertainty), leading medical physicists to implement a margin around the extents of the tumor. Reducing this uncertainty is key to improving the overall performance of the system and can dominate the accuracy of an otherwise precise system.

Prompt gammas are indirectly produced when protons interact with biological tissue and can be measured with prompt gamma cameras of varying geometries. When utilizing a slit in front of the camera, the system can capture a linear profile of how the proton beam is depositing radiation within the patient. Therefore, the prompt gamma system can be configured perpendicular to the beam path. Other variations of prompt gamma systems use an array of detectors without the slit. Spectroscopy aids in determining the type of tissue encountered by the proton beam. This improves upon typical bed-based system, where the prompt gamma detector is bed mounted or located on the gantry perpendicular to the nozzle. This can be unsatisfactory as the detector typically moves with the nozzle and patient, a complicated mechanical problem. The proposed prompt gamma detector can be configured to pivot into position after the patient has been placed into position and remain in place throughout imaging and treatment. In this way the detector does not interfere with the rotation of the patient for CBCT imaging and treatment.

Proton radiography is like photon radiography in that particles (protons) are passed through a patient, resulting in an image. Protons undergo the combined process of nuclear scattering, small angle coulomb scattering, and energy loss each with a unique dependence upon material properties. These effects make possible the simultaneous determination of both material amounts and material identification. This makes detailed characterization of the proton's behavior in the patient possible, and thus very accurate proton beam stopping power estimates. In various example embodiments of the present general inventive concept, proton radiography panels can be deployed after patient fixation, in the direct path of the beam, and removed prior to treatment. The two panels can be positioned near the patient at isocenter. Actuation is linear, simplified by the predictable upright position of the patient and fixed location of the beam path. The nozzle actuates the upstream panel and the downstream panel is actuated from the imaging ring. The concepts and methods of the present general inventive concept used to obtain raw X-ray images through the patient rotation may incorporate 2D stereoscopic imaging, 3D CBCT, proton radiography, and prompt gamma spectroscopy in a compact frame.

Figure 8A:
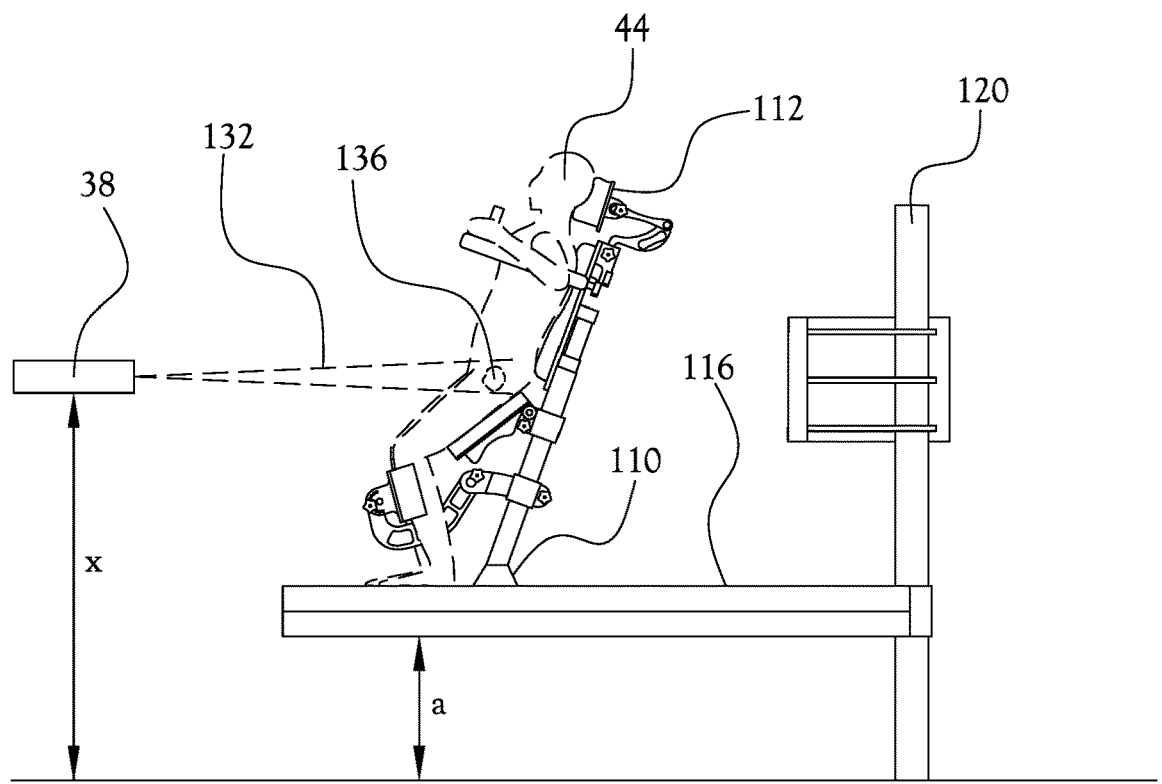
FIGS. 8A-C illustrate various positioning configurations of an upright patient positioning mechanism according to an example embodiment of the present general inventive concept.
Figure 8B:
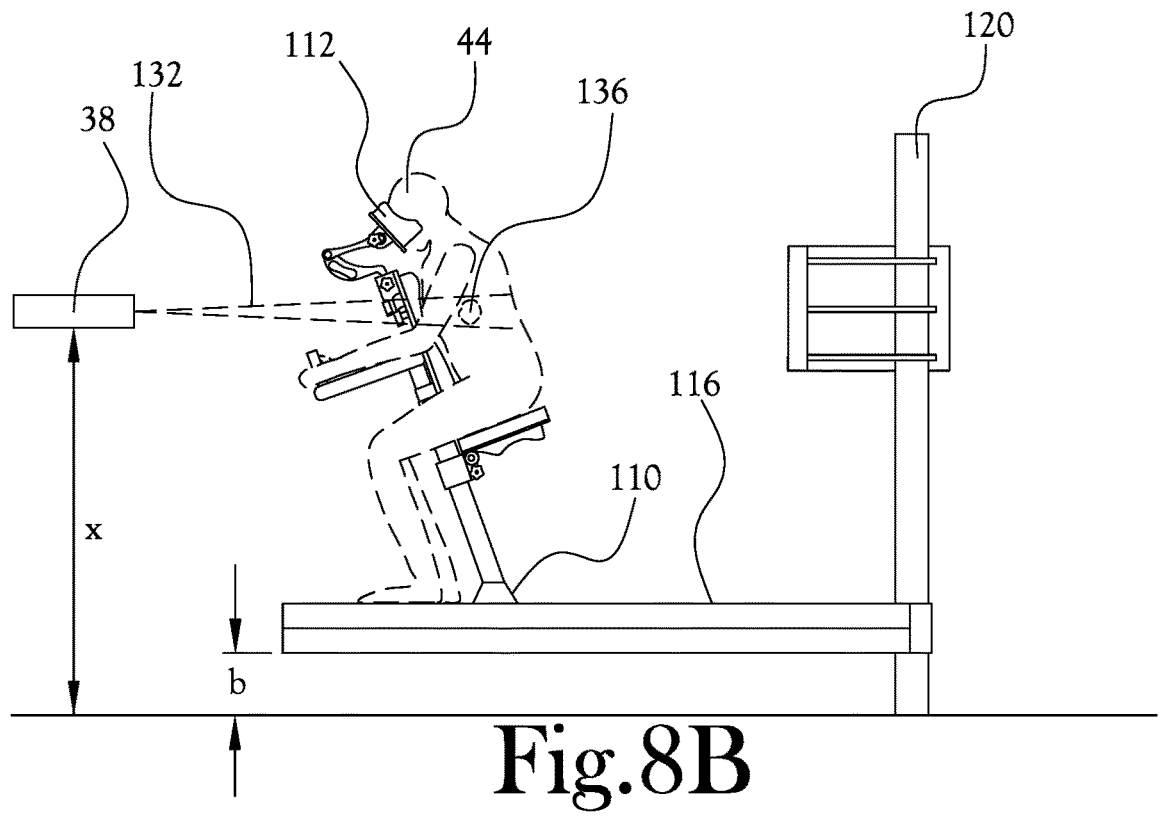
Figure 8C:
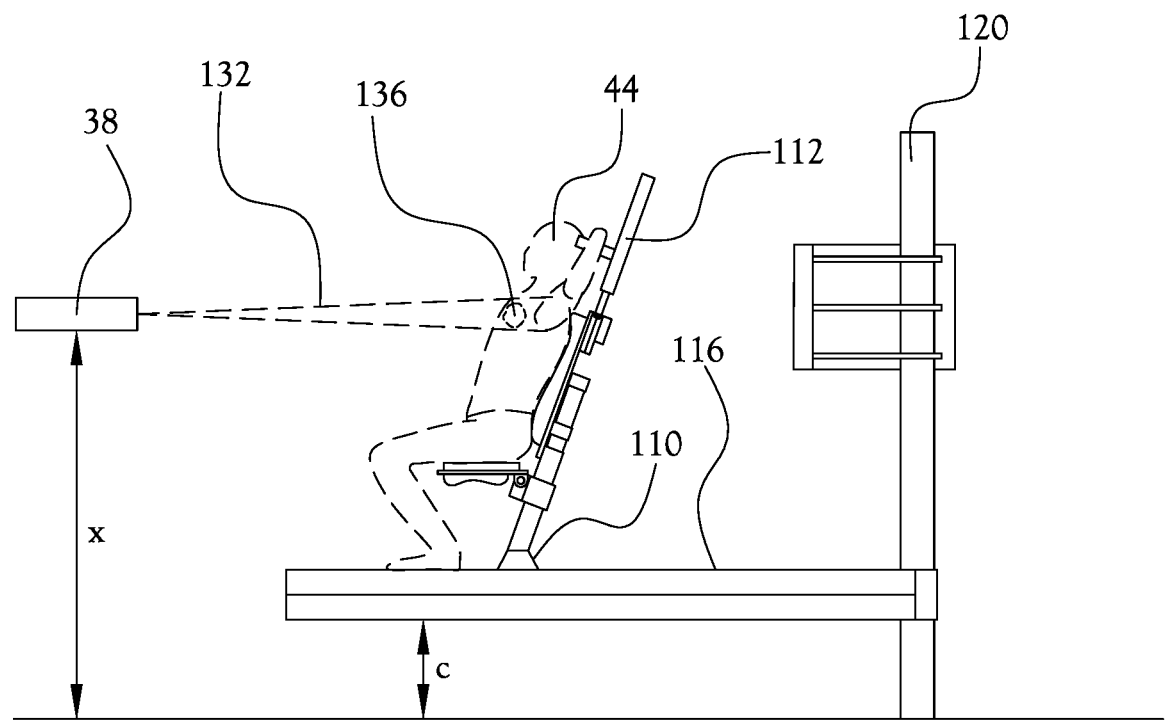
Figure 9:
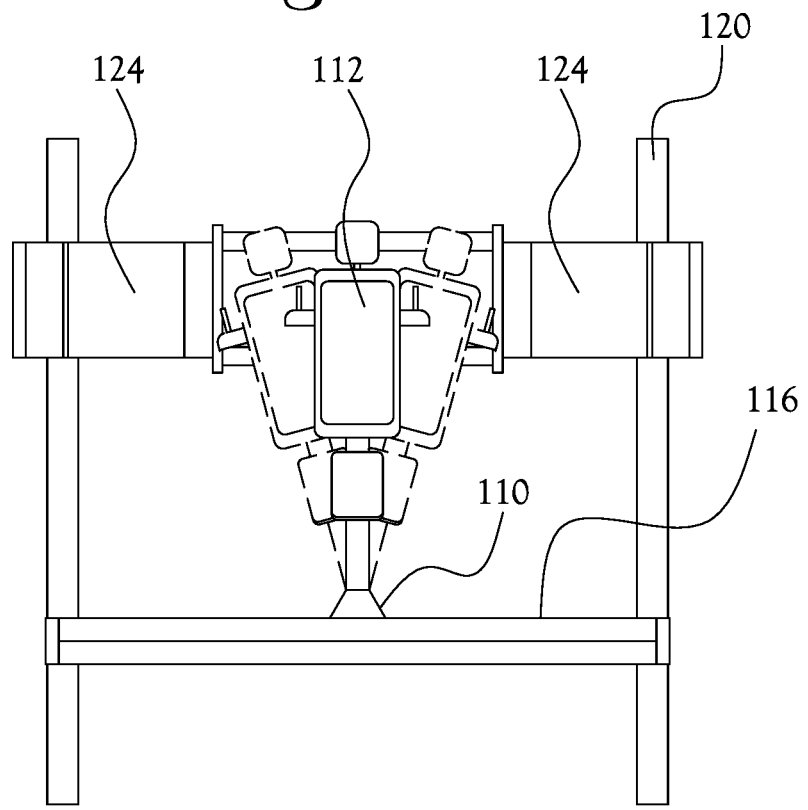
FIG. 9 illustrates some of the articulating motion capability of the patient support post of an upright patient positioning mechanism according to an example embodiment of the present general inventive concept.

FIGS. 8A-C illustrate various positioning configurations of an upright patient positioning mechanism according to an example embodiment of the present general inventive concept. FIG. 8A illustrates one type of orientation in which a patient may be positioned for treatment of, for example, a prostate tumor. FIG. 8B illustrates one type of orientation in which a patient may be positioned for treatment of, for example a lung or liver tumor. FIG. 8C illustrates one type of orientation in which a patient may be positioned for treatment of, for example, a neck tumor. As illustrated in FIGS. 8A-C, the proton beam nozzle 38 and imaging panel positions are maintained at constant heights relative to the floor of the treatment room, while the height of the movable platform 116 may be adjusted up or down, the sliding member 108 may be moved in a horizontal direction, and the patient support post 104 may be pivoted relative to the base member 100 to position the patient 44 in the desired position. FIG. 9 illustrates examples of some of the articulating motion capability of the patient support post 104 of the upright patient positioning mechanism 42 according to an example embodiment of the present general inventive concept. As illustrated in FIGS. 8A-C various patient support members 112 such as front head rests, back head rests, arm supports, seats, hand grips, knee supports, etc., may be attached to the patient support post 104 to facilitate comfortable and continued desired positioning of the patient 44.

Figure 10A:
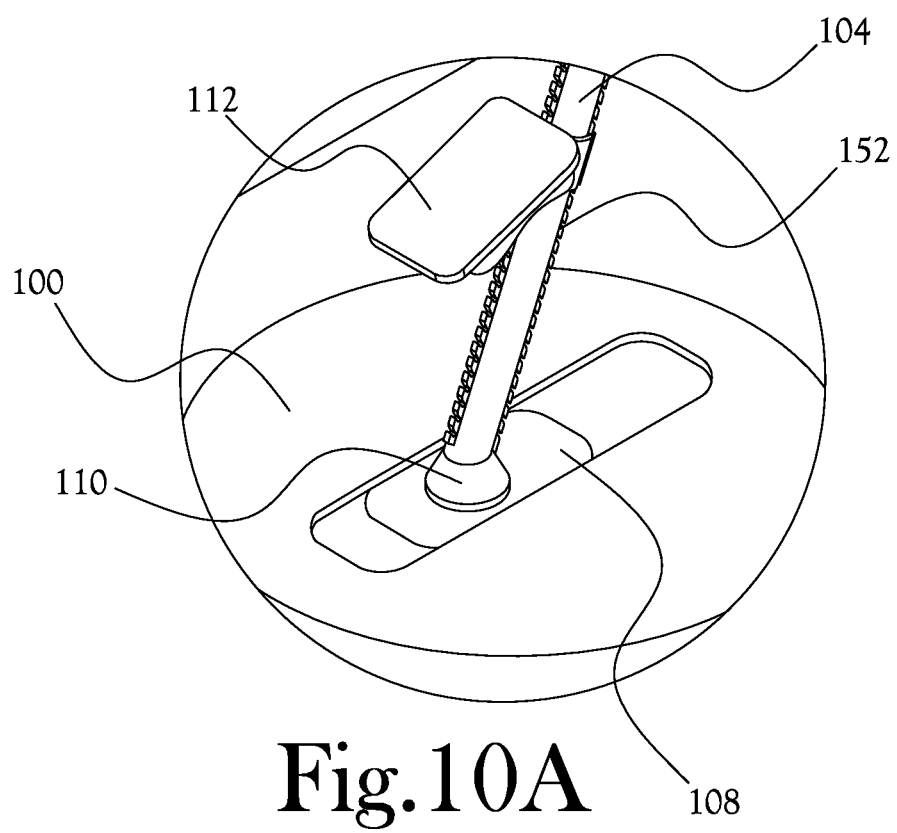
FIGS. 10A-B illustrate different surface configurations of a patient support post according to two example embodiments of the present general inventive concept.
Figure 10B:
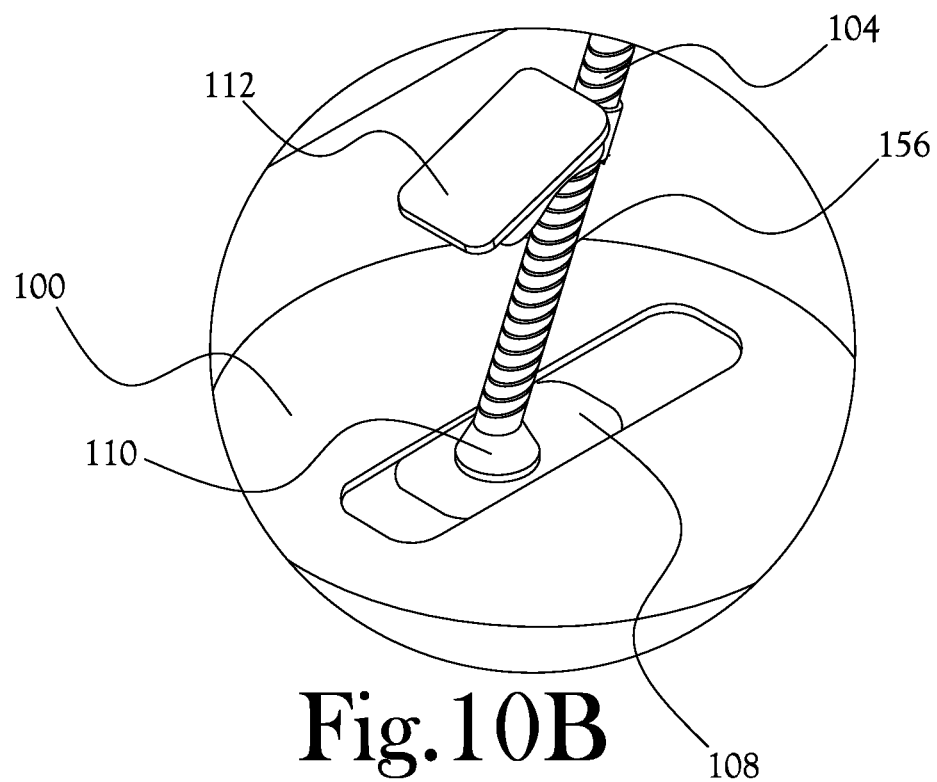

FIGS. 10A-B illustrate different surface configurations of a patient support post according to two example embodiments of the present general inventive concept. As illustrated in FIG. 10A, the patient support post 104 is provided with a series of notches 152 that are structured to receive and support corresponding male portions of a patient support member 112. As illustrated in FIG. 10B, the patient support post 104 is provided with a series of ridges 156 that surround at least a portion of the support post 104, and that are structured to receive and support corresponding portions of a patient support member 112. Such ridges may be structured as protruding members with relatively wider spaces in between the ridges, or as having relatively narrower recessed portions therebetween, and so on. It is noted that a host of other surface configurations may be formed on the patient support post 104 without departing from the scope of the present general inventive concept.

Various example embodiments of the upright patient positioning mechanism may provide a host of configurations for patient support and fixation, such as, for example: (1) seated, leaning forward with arm and head support, feet on the floor; (2) seated, leaning back with arm and head support, feet on the floor; (3) seated, leaning back with arms overhead, no head support, feet on the floor; (4) upright, leaning back with head, arm and shin support, feet on the floor; and so forth. To treat the head and neck the above described positions #1 or #2 may be used. The first position may have the patient seated with their feet on the floor leaning 20 degrees forward. The patient's face may be supported by the headrest with a custom mesh to secure the position. The arms may be wrapped forward around the support post and resting on a tray. The second position may be the same except the patient orientation may be 20 degrees backward with the arms supported on armrests. Positions #1 and #2 may have a treatment/scan area for a male whose height is approximately 185 cm (6'1") of roughly 63-69 cm. Scanning from overhead would end at approximately 66 cm from the floor. These positions may be used for treatment of the head, neck, spine, breast, chest, lung, liver and pelvis. Breast cancer could be treated utilizing position #3 with the patient seated, feet on the floor and leaning 20 degrees backwards. The armrests may be rotated up with the arms raised overhead. The breast may be positioned by using a thermo-formed support. This position may have a treatment/scan area roughly 63-69 cm on a patient whose height is approximately 185 cm (6'1"). Scanning from overhead would end at approximately 66 cm from the floor. This position could also be used for treatment of the chest and pelvis. Position #1 could be used to treat the lung and liver. Once again, the patient may be seated with their feet on the floor leaning 20 degrees forward. The patient's face may be supported by the headrest and a mesh which customizes and secures the position. The arms may be wrapped forward around the support post and rest on a tray. Position #1 may have a treatment/scan area for a male whose height is approximately 185 cm (6'1") of roughly 63-69 cm. Scanning from overhead would end at approximately 66 cm from the floor. Prostate and pelvis tumors could be treated in position #4, in which the patient has their feet on the floor and the shins are mechanically supported. The arms may be supported, as may be the head. The patient's knees may be bent slightly, and the back may be at 20 degrees, exposing the pelvis. The treatment/scan area for a male whose height is approximately 185 cm (6'1") may be 18-20 cm, and would reach the lower limit approximately 71 cm off the floor.

Technicians can use unique, easily adjustable components to safely and comfortably position the patient for scanning and treatment. In various embodiments the design of the fixation modules along with readable scales located on the support pole and other components will ensure repeatability. The use of cushions and vacuum bags along with customized mesh and thermo-forms can also be employed to complete the positioning process and adding to patient comfort. In various example embodiments the patient may be positioned in an upright position, and tilted to a reclined 20 degree angle. The inclusion of easily adjustable & removable fixation components makes the preparation easy and convenient for the attendant, and the patient can actively participate in treatment, which aids in reducing fear & anxiety. Patient immobilization is fast and repeatable. The many benefits of upright positioning include better comfort and breathing, gravity works in favor of the treatment, lower risk of asphyxiation, etc. Modular immobilization devices, support members, patient fixation accessories, etc., with a common interface makes assembly and disassembly simple and fast.

FIG. 11 illustrates the rotatable bending magnet 26 with a common housing 164 according to an example embodiment of the present general inventive concept. The rotatable bending magnet 26 can include a plurality of electromagnets 162 arranged in the common housing 164 to bend and steer the proton beam 132. One or more superconducting quadrupoles 166 can be provided upstream from the rotatable bending magnet 26. The rotatable bending magnet 26 can include the access window 46 structured to direct the proton beam 132 to the diagnostic unit 48 for various analyses before the proton beam 132 is directed to a patient treatment room.

Various example embodiments of the present general inventive concept may provide an improved proton therapy system with a small footprint and cost, improved imaging accuracy, and a flexible approach to imaging and patient fixation. Various embodiments of a complete proton therapy system can comprise two primary systems: a beamline system, including a superconducting accelerator, superconducting room switching magnets, a degrader, and a compact nozzle; and an imaging and positioning system, including an imaging array, a patient fixation assembly, a patient motion mechanism, and optional systems such as range verification, prediction, etc.

Various example embodiments of the present general inventive concept may provide a proton therapy system with components including a compact beamline and accelerator, a patient positioner, patient fixation accessories, a 90 degree bending magnet, a superconducting doublet/triplet, CBCT imaging software, prompt gamma and proton radiography, and control and planning software. Features may include upright proton treatments, a rotating bending magnet for room switching, patient rotation for 3D imaging, a modular patient fixation and support post, a polar patient positioner, and 3D volumetric imaging (CBCT). Example embodiments can be configured to operate and connect with optional modules to perform, for example, proton radiotherapy, prompt gamma detection, etc., and can be configured to interact with other patient mechanisms such as beds and imagers, alternative patient fixation devices, etc. Many of the components may be combined and configured to minimize the building footprint, reduce cost, and expand clinical capabilities.

According to various example embodiments of the present general inventive concept, the compact beamline can be centered upon superconducting technology, reducing the overall footprint of the accelerator. The accelerator may be configured to possess excellent beam properties to minimize the focusing and beam manipulation length. The beamline of the treatment system may comprise three sections: extraction beamline (EXTBL), SC achromat beamline (SCABL), and normal conducting beamline (NCBL). In some embodiments the EXTBL can deliver a proton beam out of SCIC onto a degrader at a fixed energy of 230 MeV; SCABL can be a 90 degree achromat made up of SC dipole and quadrupole magnets, and NCBL can include 4 normal conducting quadrupoles and a scanning magnet. SCIC can extract a proton beam at a fixed energy of 230 MeV, and a degrader can modulate the beam energy to desired ranges, for example from 4 to 32 cm. EXTBL can focus and center the beam onto the degrader and provide the maximum beam transmission to the downstream beamline. The 90 degree achromat SCABL can select and transport the proton beam of the right energy and emittance to NCBL for final beam focusing and wide field scanning; essential for precise treatments. Because neutron fluxes generated in the degrader are perpendicular to the downstream beamline, unwanted neutron radiation to patients will be minimized. To reduce the amount of shielding, the system can include independent degraders disposed in each treatment room downstream of the switching magnet, but it is possible to use a single degrader disposed proximate an outlet of the accelerator upstream of the switching magnet. The system can be configured in shape and size to fit within an existing two LINAC vault.

Regarding facilities for proton treatment systems of the present general inventive concept, the compact proton system can be configured to fit within the footprint and height of an existing mazed two room LINAC vault (e.g., 80'×36'). New installations can receive an identical or similar footprint, with modifications to the shielding details. High density block can be stacked within the existing vault footprint for additional shielding. Depending on site conditions, a hatch may not be necessary or practical. The cyclotron and primary beamline may be installed through the southern exterior wall with post installed high density shielding block. The patient fixation and imager can be transported and installed through the existing building shell. Sliding shielding doors may be utilized to achieve a small footprint and maintain workflow. An interior curtain wall may be provided to separate the electrical enclosures from the clinical space. Such a curtain wall can have locked doors and provide the space for all electrical enclosures, and in most instances no additional power supply room is anticipated. The compact system can be configured to fit into the footprint of a mazed two room LINAC vault. The compact beamline and accelerator can fit in the space reserved for the maze, and a compact rotating 90 degrees bending magnet can divert the beam between rooms 1 and 2. A bend is used to minimize neutron dose to the patient. A compact 90 degree bend fits well into the right angles of a building.

Shielding estimates show may indicate three critical areas for various example embodiments. Downstream of degrader, the majority of the radiation exposure is due to energy reduction at the degrader. The compact 90 degree layout ensures that this radiation is not directed toward the patient, instead going to a 6'+ thick local shielding wall. This shielding wall may have additional space allocated for site specific shielding requirements. Downstream of patient, the patient receives radiation and the downstream neutrons may be managed by installation of high density stacked block. Additional thickness may be accommodated in this area without reducing workspace around the patient. Moveable shielding doors may be provided, and the overlapping areas around the shielding doors can be configured with blocks to ensure that errant beams are managed. The overlap can be in the direction of a high occupancy area, likely a control or patient set-up room.

Various example embodiments of the present general inventive concept may provide a proton treatment system including a proton accelerator structured to generate a proton beam, a plurality of beamline pathways configured to direct the proton beam from the proton accelerator to a corresponding plurality of treatment rooms, a rotatable bending magnet located between the proton accelerator and the plurality of treatment rooms, the rotatable bending magnet being structured to selectively rotate between a first position and a second position such that when the rotatable bending magnet is rotated to the first position, the rotatable bending magnet directs the proton beam to a first treatment room, and when the rotatable bending magnet is rotated to the second position, the rotatable bending magnet directs the proton beam to a second treatment room, a plurality of proton delivery nozzles located downstream of the rotatable bending magnet within each treatment room and structured to direct the proton beam to a fixed location within each treatment room, respectively, and an upright patient positioning mechanism disposed in each of the treatment rooms, the upright patient positioning mechanism being structured to support a patient within a particular treatment room such that the fixed location of the particular treatment room is located at an isocenter of a target area of the patient when the proton beam is delivered to the particular treatment room. The proton accelerator may be configured to direct the proton beam in a substantially vertical direction with respect to the floor of the plurality of treatment rooms, and the rotatable bending magnet may be arranged so as to bend the proton beam approximately 90 degrees with respect to the vertical direction so as to direct the proton beam to a selected one of the plurality of treatment rooms. The proton accelerator may be configured to direct the proton beam in a substantially horizontal plane relative to the floor of the plurality of treatment rooms, and the rotatable bending magnet may be structured to selectively bend the proton beam approximately 90 degrees on the substantially horizontal plane to selectively direct the proton beam into one of the first and second treatment rooms. The rotatable bending magnet may include an access window structured to selectively allow the proton beam to pass through the rotatable bending magnet without changing a direction of the proton beam. The system may further include a diagnostic unit structured to measure one or more characteristics of the proton beam when the proton beam passes through the access window. The upright patient positioning mechanism may include a base member structured to rotate about the isocenter of the target area, and a patient support post structured to extend upward from the base member, and to be pivotable with respect to the base member. The upright patient positioning mechanism further includes a sliding member positioned on the base member and structured to be reciprocally movable with respect to the base member, wherein the upright patient support post is removably attachable to the sliding member. The upright patient support post may be configured to receive one or more support members structured to support various body parts of the patient. The upright patient support post may be formed with ridges and/or notches on an outer surface thereof structured to secure portions of the one or more support members received therein. The upright patient support post may be formed with a series of ridges formed along an outer surface to support portions of the one or more support members affixed to the upright patient support post. The one or more support members may include a seat, knee support, arm rest, handles, head rest, or any combination thereof. The upright patient positioning mechanism may further include a movable platform structured to support the base member and to be selectively raised and lowered relative to the fixed location. The upright patient positioning mechanism may further include at least two vertical columns structured to support the movable platform, the movable platform being structured to be selectively moveable up and down along the vertical columns. The system may further include a plurality of imaging sources structured to scan the target area of the patient, and a plurality of imaging panels structured to cooperate with the imaging sources to form an image of the target area. The imaging sources may be fixed to a wall in the treatment room through which the proton beam passes. The imaging panels may be selectively moveable relative to the imaging sources. The system may further include a prompt gamma detector that is selectively movable to and from a deployed position proximate the patient positioning mechanism and perpendicular to the proton beam. The system may further include a first proton radiography panel selectively positionable upstream of the proton beam relative to the patient, and a second proton radiography panel selectively positionable downstream of the proton beam relative to the patient. The system may further include a selectively movable platform structured to support the upright patient positioning mechanism, and a plurality of vertical columns structured to support the movable platform, the movable platform being structured to be selectively slidable up and down along the vertical columns, wherein one or more of the imaging panels, prompt gamma detector, and proton radiography panels may be connected to one or more of the plurality of vertical columns. The rotatable bending magnet may include a movement mechanism to selectively rotate the rotatable bending magnet to direct the proton beam to a diagnostic unit rather than to one of the treatment rooms.

Various example embodiments of the present general inventive concept may provide a rotating bending magnet assembly for use in a proton treatment system, including an achromatic superconducting magnet configured to change the direction of a proton beam by approximately 90 degrees, and a movement mechanism structured to rotate the achromatic superconducting magnet so as to selectively direct the proton beam in a first direction or a second direction, where the first direction is opposite to the second direction. The achromatic superconducting magnet may be housed within a common housing.

Various example embodiments of the present general inventive concept may provide a proton treatment system including a proton accelerator structured to generate a proton beam, a plurality of beamline pathways configured to direct the proton beam from the proton accelerator to a corresponding plurality of treatment rooms, a rotatable bending magnet located between the proton accelerator and the plurality of treatment rooms, the rotatable bending magnet being structured to selectively rotate between a first position and a second position such that when the rotatable bending magnet is rotated to the first position, the rotatable bending magnet directs the proton beam to a first treatment room, and when the rotatable bending magnet is rotated to the second position, the rotatable bending magnet directs the proton beam to a second treatment room, and a plurality of proton delivery nozzles located downstream of the rotatable bending magnet within each treatment room and structured to direct the proton beam to a fixed location within each treatment room, respectively.

Various example embodiments of the present general inventive concept may provide an upright positioning mechanism to be used with a proton treatment system, the upright positioning mechanism including a base member structured to rotate about an isocenter of a target area of a patient, and a patient support post structured to extend upward from the base member, and to be pivotable with respect to the base member, wherein the upright patient positioning mechanism is structured to support the patient and provide six degrees of freedom in movement within a treatment room such that a fixed line proton beam is delivered to the isocenter of the target area of the patient.

Various example embodiments of the present general inventive concept may provide a method of, and/or a means for, performing three-dimensional image reconstruction during proton treatment of a patient by rotating a patient between a fixed imaging source and imaging panel, generating a series of images of a target area of the patient, and reconstructing the images into three-dimensional volumetric representations.

Various example embodiments of the present general inventive concept may provide a proton radiotherapy system including a proton accelerator, a switching magnet disposed downstream of a beamline(s), an upright patient positioner, one or more patient fixation devices attached to a central support, a patient positioning mechanism, a fixed imaging array, and an apparatus for rotating the patient about an isocenter. The switching magnet may be a rotating bending magnet including an achromatic superconducting magnet, and a mechanism for rotating a magnet assembly about a beam axis. The rotating bending magnet may include a resistive achromat. Two or more beamlines may be arranged in one of a collinear fashion with respect to one another, or a radial fashion with respect to the proton accelerator. The two or more beamlines may be arranged at predetermined angles relative to one another and to the proton accelerator. Various example embodiments of the present general inventive concept may provide a method of using such a system of claim 1, the method including compactly arranging at least one accelerator beamline and at least two patient delivery beamlines such that the at least one accelerator beamline is oriented perpendicular to the at least two patient delivery beamlines and the at least two patient delivery beamlines are oriented collinear to one another and in opposing directions. The proton accelerator beamline and the at least two patient delivery beamlines may be arranged at right angles forming a T. The switching magnet may be a rotating superconducting magnet centrally located between the at least two patient delivery beamlines such that rotation of the rotating superconducting magnet selectively diverts a proton beam from one of the at least two patient delivery beamlines to another. A method of using such a system may include arranging two or more beamlines with respect to the proton accelerator, and the two or more beamlines may be arranged at predetermined angles relative to one another and to the proton accelerator. A method of using such a system may include switching the switching magnet to selectively deliver a proton beam to multiple treatment locations via multiple beamlines.

Various example embodiments of the present general inventive concept may provide a proton radiotherapy system including a plurality of fixed beamlines, an upright patient support, and a mechanized baseframe, static X-ray source, and panels, wherein a patient in the patient support is rotated relative to a beam axis for three dimensional image construction, and wherein the mechanized baseframe is used to rotate the patient precisely about an isocenter and provide for locating a target in the beam axis. The target may be a tumor or any lesion that needs radiation therapy treatment in the patient. The upright patient support may be configured as a patient fixation and positioning device with an upright and central patient support, and the system may further include an upright positioning device; and various patient support devices, wherein said mechanized baseframe accepts the upright positioning device by means of quick release mechanism, and wherein the various patient support devices are easily attached to the upright patient support by means of a common interface to allow for positioning the patient in a forward or backward leaning position. The patient fixation and positioning device may include a central pole with embedded pins or teeth, wherein the patient support devices may be secured to the pins or teeth by gravity. The mechanized baseframe may include a patient walking platform, a rotating turntable, a linear slide, a rotating gimbal, and an interface attachment for various patient supports, wherein the linear slide, rotating gimbal, and interface attachment may be housed within an envelope of the rotating turntable.

The mechanized baseframe may include a vertical support structure and a carriage mechanism, wherein the mechanized baseframe may be attached to the carriage mechanism and vertical support structure so as to permit vertical motion of the patient, and the vertical support structure and a primary axis of rotation may be eccentric. The vertical support structure may be configured to support imaging modalities around the patient and to align the imaging modalities in a static manner to the primary iso-axis of rotation. The imaging modalities may include, but are not limited to, planar x-rays, cone beam CT, proton radiography, prompt gamma, optical tracking, and PET panels. The imaging of a target area may occur simultaneous with treatment of the target area and without interrupting or interfering with the proton treatment beam.

Various example embodiments of the present general inventive concept may provide a method of generating three dimensional images for cone beam CT, the method including rotating a patient between a fixed x-ray source and panel, generating a series of images, and reconstructing the images into volumetric representations. The method may include the use of optical tracking, surface tracking, ultrasound, or other imaging tools. The method may further include using the images to monitor patient and/or target position in real time during treatment. The system may include independent degraders disposed for each treatment room downstream of the switching magnet. The system may include a single degrader disposed proximate an outlet of the accelerator upstream of the switching magnet. The system may be configured to fit within an existing two LINAC vault.

As illustrated and described herein, the proton treatment arrangement can include a compact beamline with a single switching magnet that diverts beam into 2 or more treatment rooms. The treatment rooms can be compact, housing a patient positioner which places the patient torso in a near upright position and rotates about a vertical axis for various beam angles. Using the ability to rotate, static imaging devices such as x-ray panels and x-ray sources or a host of other imaging components can be used to generate a series of images which are then used to reconstruct a three-dimensional image. The patient motion can be accomplished through a pedestal attached to a vertical support frame. The entire pedestal can translate vertically on the frame. The positioning mechanism can have capability for placing the patient in the remaining 5 degrees of freedom. The motion elements can be housed within the envelope of the base and can be terminated by a connection interface for which a series of modular patient supports may be attached. The patient support can include a central pole or rib which attaches to the baseplate by means of a connection interface. In some example embodiments the patient can either straddle (forward facing) or lean back against the pole for support. Patient fixation attachments can be mounted to the central pole by means of a common interface.

As described, the systems, apparatus, methods, processes, functions, and/or operations for implementing the example embodiments of the present general inventive concept may be wholly or partially implemented in the form of apparatus that includes processing elements and sets of executable instructions. The executable instructions may be part of one or more software applications and arranged into software architecture. In general, embodiments of the present general inventive concept may be implemented using a set of software instructions that are designed to be executed by a suitably programmed processing element (such as a CPU, GPU (graphics processing unit), microprocessor, processor, controller, computing device, etc.). In a complex application or system such instructions are typically arranged into "modules" with each such module typically performing a specific task, process, function, or operation. The entire set of modules may be controlled or coordinated in their operation by an operating system (OS) or other form of organizational platform.

The application modules may include any suitable computer-executable code or set of instructions (e.g., as would be executed by a suitably programmed processor, microprocessor, or CPU), such as computer-executable code corresponding to a programming language. For example, programming language source code may be compiled into computer-executable code. Alternatively, or in addition, the programming language may be an interpreted programming language such as a scripting language. The computer-executable code or set of instructions may be stored in (or on) any suitable non-transitory computer-readable medium. In general, with regards to the embodiments described herein, a non-transitory computer-readable medium may include almost any structure, technology or method apart from a transitory waveform or similar medium.

As described, the systems, apparatus, methods, processes, functions, and/or operations for implementing the example embodiments of the present general inventive concept may be wholly or partially implemented in the form of a set of instructions executed by one or more programmed computer processors such as a central processing unit (CPU) or microprocessor. Such processors may be incorporated in the circuitry and components of an apparatus, server, client or other computing or data processing device operated by, or in communication with, other components of the system.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components, processes or functions described in this application may be implemented as software code to be executed by a processor using any suitable computer language such as, for example, Java, JavaScript, C++ or Perl using, for example, conventional or object-oriented techniques. The software code may be stored as a series of instructions, or commands in (or on) a non-transitory computer-readable medium, such as a random-access memory (RAM), a read only memory (ROM), a magnetic medium such as a hard-drive or a floppy disk, or an optical medium such as a CD-ROM. In this context, a non-transitory computer-readable medium is almost any medium suitable for the storage of data or an instruction set aside from a transitory waveform. Any such computer readable medium may reside on or within a single computational apparatus, and may be present on or within different computational apparatuses within a system or network.

According to some example implementations, the term processing element or processor, as used herein, may be a central processing unit (CPU), or conceptualized as a CPU (such as a virtual machine). In such example implementation, the CPU or a device in which the CPU is incorporated may be coupled, connected, and/or in communication with one or more peripheral devices such as the movement mechanisms, as well as one or more displays. In other example implementations, the processing element or processor may be incorporated into a mobile computing device, such as a smartphone or tablet computer.

The non-transitory computer-readable storage medium referred to herein may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, synchronous dynamic random access memory (SDRAM), or similar devices or other forms of memories based on similar technologies. Such computer-readable storage media allow the processing element or processor to access computer-executable process steps, application programs and the like, stored on removable and non-removable memory media, to off-load data from a device or to upload data to a device. As mentioned, with regards to the embodiments described herein, a non-transitory computer-readable medium may include almost any structure, technology or method apart from a transitory waveform or similar medium.

Certain implementations of the disclosed technology are described herein with reference to block diagrams of systems, and/or to configurations, functions, processes, or methods. It will be understood that one or more of the configurations, methods, processes, and functions can be implemented by computer-executable program instructions. Note that in some embodiments, one or more of the configurations, methods, processes, and functions may not necessarily need to be performed in a particular order, or may not necessarily need to be performed at all.

These computer-executable program instructions may be loaded onto a general-purpose computer, a special purpose computer, a processor, or other programmable data processing apparatus to produce a specific example of a machine, such that the instructions that are executed by the computer, processor, or other programmable data processing apparatus create means for implementing one or more of the functions, operations, processes, or methods described herein. These computer program instructions may also be stored in a computer-readable memory that can direct a computer or other programmable data processing apparatus to function in a specific manner, such that the instructions stored in the computer-readable memory produce an article of manufacture including instruction means that implement one or more of the functions, operations, processes, or methods described herein.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein, using sound engineering judgment. Numerous variations, modification, and additional embodiments are possible, and, accordingly, all such variations, modifications, and embodiments are to be regarded as being within the spirit and scope of the present general inventive concept.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

The invention claimed is:

1. A proton treatment system, comprising:
a proton accelerator structured to generate a proton beam;
a plurality of beamline pathways configured to direct the proton beam from the proton accelerator to a corresponding plurality of treatment rooms;
a rotatable bending magnet located between the proton accelerator and the plurality of treatment rooms, the rotatable bending magnet being structured to selectively rotate between a first position and a second position such that when the rotatable bending magnet is rotated to the first position, the rotatable bending magnet directs the proton beam to a first treatment room, and when the rotatable bending magnet is rotated to the second position, the rotatable bending magnet directs the proton beam to a second treatment room;
a plurality of proton delivery nozzles located downstream of the rotatable bending magnet within each treatment room and structured to direct the proton beam to a fixed location within each treatment room, respectively; and
an upright patient positioning mechanism disposed in each of the treatment rooms, the upright patient positioning mechanism being structured to support a patient within a particular treatment room such that the fixed location of the particular treatment room is located at an isocenter of a target area of the patient when the proton beam is delivered to the particular treatment room.

2. The system of claim 1, wherein the proton accelerator is configured to direct the proton beam in a substantially vertical direction with respect to the floor of the plurality of treatment rooms; and
wherein the rotatable bending magnet is arranged so as to bend the proton beam approximately 90 degrees with respect to the vertical direction so as to direct the proton beam to a selected one of the plurality of treatment rooms.

3. The system of claim 1, wherein the proton accelerator is configured to direct the proton beam in a substantially horizontal plane relative to the floor of the plurality of treatment rooms; and
wherein the rotatable bending magnet is structured to selectively bend the proton beam approximately 90 degrees on the substantially horizontal plane to selectively direct the proton beam into one of the first and second treatment rooms.

4. The system of claim 1, wherein the rotatable bending magnet comprises an access window structured to selectively allow the proton beam to pass through the rotatable bending magnet without changing a direction of the proton beam.

5. The system of claim 4, further comprising a diagnostic unit structured to measure one or more characteristics of the proton beam when the proton beam passes through the access window.

6. The system of claim 1, wherein the upright patient positioning mechanism comprises:
   a base member structured to rotate about the isocenter of the target area; and
   a patient support post structured to extend upward from the base member, and to be pivotable with respect to the base member.

7. The system of claim 6, wherein the upright patient positioning mechanism further comprises:
   a sliding member positioned on the base member and structured to be reciprocally movable with respect to the base member, wherein the upright patient support post is removably attachable to the sliding member.

8. The system of claim 6, wherein the upright patient support post is configured to receive one or more support members structured to support various body parts of the patient.

9. The system of claim 8, wherein the upright patient support post is formed with ridges and/or notches on an outer surface thereof structured to secure portions of the one or more support members received therein.

10. The system of claim 8, wherein the upright patient support post is formed with a series of ridges formed along an outer surface to support portions of the one or more support members affixed to the upright patient support post.

11. The system of claim 8, wherein the one or more support members include a seat, knee support, arm rest, handles, head rest, or any combination thereof.

12. The system of claim 6, wherein the upright patient positioning mechanism further comprises a movable platform structured to support the base member and to be selectively raised and lowered relative to the fixed location.

13. The system of claim 12, wherein the upright patient positioning mechanism further comprises at least two vertical columns structured to support the movable platform, the movable platform being structured to be selectively moveable up and down along the vertical columns.

14. The system of claim 1, further comprising:
   a plurality of imaging sources structured to scan the target area of the patient; and
   a plurality of imaging panels structured to cooperate with the imaging sources to form an image of the target area.

15. The system of claim 14, wherein the imaging sources are fixed to a wall in the treatment room through which the proton beam passes.

16. The system of claim 15, wherein the imaging panels are selectively moveable relative to the imaging sources.

17. The system of claim 14, further comprising a prompt gamma detector that is selectively movable to and from a deployed position proximate the patient positioning mechanism and perpendicular to the proton beam.

18. The system of claim 17, further comprising:
   a first proton radiography panel selectively positionable upstream of the proton beam relative to the patient; and
   a second proton radiography panel selectively positionable downstream of the proton beam relative to the patient.

19. The system of claim 18, further comprising:
   a selectively movable platform structured to support the upright patient positioning mechanism; and
   a plurality of vertical columns structured to support the movable platform, the movable platform being structured to be selectively slidable up and down along the vertical columns;
   wherein one or more of the imaging panels, prompt gamma detector, and proton radiography panels are connected to one or more of the plurality of vertical columns.

20. The system of claim 1, wherein the rotatable bending magnet includes a movement mechanism to selectively rotate the rotatable bending magnet to direct the proton beam to a diagnostic unit rather than to one of the treatment rooms.

21. A rotating bending magnet assembly for use in a proton treatment system, comprising:
   an achromatic superconducting magnet configured to change the direction of a proton beam by approximately 90 degrees; and
   a movement mechanism structured to rotate the achromatic superconducting magnet so as to selectively direct the proton beam in a first direction or a second direction, where the first direction is opposite to the second direction.

22. The assembly of claim 21, wherein the achromatic superconducting magnet is housed within a common housing.

23. A proton treatment system, comprising:
   a proton accelerator structured to generate a proton beam;
   a plurality of beamline pathways configured to direct the proton beam from the proton accelerator to a corresponding plurality of treatment rooms;
   a rotatable bending magnet located between the proton accelerator and the plurality of treatment rooms, the rotatable bending magnet being structured to selectively rotate between a first position and a second position such that when the rotatable bending magnet is rotated to the first position, the rotatable bending magnet directs the proton beam to a first treatment room, and when the rotatable bending magnet is rotated to the second position, the rotatable bending magnet directs the proton beam to a second treatment room; and
   a plurality of proton delivery nozzles located downstream of the rotatable bending magnet within each treatment room and structured to direct the proton beam to a fixed location within each treatment room, respectively.

\* \* \* \* \*